(12) United States Patent
Karmon

(10) Patent No.: US 11,819,380 B2
(45) Date of Patent: Nov. 21, 2023

(54) DEVICES FOR TISSUE AUGMENTATION

(71) Applicant: Ben Zion Karmon, Petach-Tikva (IL)

(72) Inventor: Ben Zion Karmon, Petach-Tikva (IL)

( * ) Notice: Subject to any disclaimer, the term of this patent is extended or adjusted under 35 U.S.C. 154(b) by 1108 days.

(21) Appl. No.: 16/340,351

(22) PCT Filed: Oct. 2, 2017

(86) PCT No.: PCT/IL2017/051113
§ 371 (c)(1),
(2) Date: Apr. 8, 2019

(87) PCT Pub. No.: WO2018/069918
PCT Pub. Date: Apr. 19, 2018

(65) Prior Publication Data
US 2019/0274790 A1 Sep. 12, 2019

(30) Foreign Application Priority Data
Oct. 13, 2016 (IL) .......................................... 248472

(51) Int. Cl.
  *A61C 8/02* (2006.01)
  *A61F 2/28* (2006.01)
  *A61F 2/30* (2006.01)

(52) U.S. Cl.
  CPC .......... *A61C 8/0006* (2013.01); *A61F 2/2803* (2013.01); *A61F 2/2846* (2013.01); *A61F 2002/30011* (2013.01); *A61F 2002/30028* (2013.01); *A61F 2002/30235* (2013.01); *A61F 2002/30448* (2013.01); *A61F 2002/30461* (2013.01); *A61F 2002/30581* (2013.01); *A61F 2002/30594* (2013.01); *A61F 2002/30784* (2013.01); *A61F 2310/00371* (2013.01)

(58) Field of Classification Search
None
See application file for complete search history.

(56) References Cited

U.S. PATENT DOCUMENTS

| 3,640,278 A | 2/1972 | Benjamin |
| 3,800,788 A | 4/1974 | White |
| 3,875,595 A | 4/1975 | Froning |
| 3,924,274 A | 12/1975 | Heimke et al. |

(Continued)

FOREIGN PATENT DOCUMENTS

| CN | 1125559 A | 7/1996 |
| DE | 4321785 C1 | 3/1995 |

(Continued)

OTHER PUBLICATIONS

Notice of Reasons for Refusal in Japanese patent application No. 2019-520092 from Japanese Patent Office filed on Nov. 9, 2021.

(Continued)

*Primary Examiner* — Brian A Dukert
*Assistant Examiner* — Melissa A Hoban

(57) ABSTRACT

Devices, method to produce devices and methods to perform bone augmentation using a bag having two membranes on one side and one membrane on the other side which is preferably perforated. The bag can be filled with bone augmenting material. The bag can be used in the jaws while placing the side with the one membrane towards the jaw bone and the side with the two membranes towards the gingiva.

20 Claims, 3 Drawing Sheets

(56) References Cited

U.S. PATENT DOCUMENTS

| | | |
|---|---|---|
| 4,313,434 A | 2/1982 | Segal |
| 4,430,760 A | 2/1984 | Smestad |
| 4,431,416 A | 2/1984 | Niznick |
| 4,501,266 A | 2/1985 | McDaniel |
| 4,521,192 A | 6/1985 | Linkow |
| 4,627,434 A | 12/1986 | Murray |
| 4,653,489 A | 3/1987 | Tronzo |
| 4,665,918 A | 5/1987 | Garza et al. |
| 4,682,951 A | 7/1987 | Linkow |
| 4,686,985 A | 8/1987 | Lottick |
| 4,690,684 A | 9/1987 | McGreevy et al. |
| 4,740,207 A | 4/1988 | Kreamer |
| 4,744,754 A | 5/1988 | Ross |
| 4,755,184 A | 7/1988 | Silverberg |
| 4,768,507 A | 9/1988 | Fischell et al. |
| 4,787,906 A | 11/1988 | Haris |
| 4,798,205 A | 1/1989 | Bonomo et al. |
| 4,824,436 A | 4/1989 | Wolinski |
| 4,832,688 A | 5/1989 | Sagae et al. |
| 4,843,112 A | 6/1989 | Gerhart et al. |
| 4,863,472 A | 9/1989 | Tormala et al. |
| 4,878,906 A | 11/1989 | Lindemann et al. |
| 4,922,905 A | 5/1990 | Strecker |
| 4,929,247 A | 5/1990 | Rayhack |
| 4,950,227 A | 8/1990 | Savin et al. |
| 4,969,888 A | 11/1990 | Scholten et al. |
| 4,994,298 A | 2/1991 | Yasuda |
| 5,005,591 A | 4/1991 | Austad |
| 5,020,525 A | 6/1991 | Ewing et al. |
| 5,059,194 A | 10/1991 | Michelson |
| 5,102,413 A | 4/1992 | Poddar |
| 5,108,404 A | 4/1992 | Scholten et al. |
| 5,108,416 A | 4/1992 | Ryan et al. |
| 5,146,933 A | 9/1992 | Boyd |
| 5,152,747 A | 10/1992 | Olivier |
| 5,156,605 A | 10/1992 | Pursley et al. |
| 5,158,548 A | 10/1992 | Lau et al. |
| 5,180,380 A | 1/1993 | Pursley et al. |
| 5,192,307 A | 3/1993 | Wall |
| 5,234,457 A | 8/1993 | Andersen |
| 5,242,399 A | 9/1993 | Lau et al. |
| 5,254,089 A | 10/1993 | Wang |
| 5,286,261 A | 2/1994 | Roizenblatt |
| 5,304,117 A | 4/1994 | Wilk |
| 5,306,286 A | 4/1994 | Stack et al. |
| 5,308,350 A | 5/1994 | Mikhail |
| 5,350,580 A * | 9/1994 | Muchow .............. A61K 9/7007 514/956 |
| 5,372,583 A | 12/1994 | Roberts et al. |
| 5,376,123 A | 12/1994 | Klaue et al. |
| 5,380,329 A | 1/1995 | Elia et al. |
| 5,397,235 A | 3/1995 | Elia |
| 5,405,322 A | 4/1995 | Lennox et al. |
| 5,423,885 A | 6/1995 | Williams |
| 5,429,638 A | 7/1995 | Muschler et al. |
| 5,439,446 A | 8/1995 | Barry |
| 5,441,515 A | 8/1995 | Khosravi et al. |
| 5,443,500 A | 8/1995 | Sigwart |
| 5,480,400 A | 1/1996 | Berger |
| 5,487,897 A | 1/1996 | Polson et al. |
| 5,496,368 A | 3/1996 | Wiese |
| 5,505,733 A | 4/1996 | Justin et al. |
| 5,511,565 A | 4/1996 | Syers |
| 5,514,137 A | 5/1996 | Coutts |
| 5,536,269 A | 7/1996 | Spievack |
| 5,547,378 A | 8/1996 | Linkow |
| 5,549,676 A | 8/1996 | Johnson |
| 5,549,679 A | 8/1996 | Kuslich |
| 5,562,736 A | 10/1996 | Ray et al. |
| 5,569,308 A | 10/1996 | Sottosanti |
| 5,571,189 A | 11/1996 | Kuslich |
| 5,630,843 A | 5/1997 | Rosenberg |
| 5,655,545 A | 8/1997 | Johnson et al. |
| 5,674,295 A | 10/1997 | Ray et al. |
| 5,676,664 A | 10/1997 | Allard et al. |
| 5,676,699 A | 10/1997 | Gogolewski et al. |
| 5,681,309 A | 10/1997 | Ross, Jr. et al. |
| 5,685,716 A | 11/1997 | Linkow |
| 5,695,338 A | 12/1997 | Robert |
| 5,700,479 A | 12/1997 | Lundgren |
| 5,704,939 A | 1/1998 | Justin |
| 5,711,315 A | 1/1998 | Jerusalmy |
| 5,741,223 A | 4/1998 | Janzen et al. |
| 5,746,762 A | 5/1998 | Bass |
| 5,766,173 A | 6/1998 | Ross, Jr. et al. |
| 5,769,856 A | 6/1998 | Dong et al. |
| 5,772,661 A | 6/1998 | Michelson |
| 5,779,728 A | 7/1998 | Lunsford et al. |
| 5,792,400 A | 8/1998 | Talja et al. |
| 5,807,382 A | 9/1998 | Chin |
| 5,810,812 A | 9/1998 | Chin |
| 5,827,289 A | 10/1998 | Reiley et al. |
| 5,839,899 A | 11/1998 | Robinson |
| 5,857,998 A | 1/1999 | Barry |
| 5,873,715 A | 2/1999 | Liou |
| 5,882,353 A | 3/1999 | VanBeek et al. |
| 5,895,387 A | 4/1999 | Guerrero et al. |
| 5,902,304 A | 5/1999 | Walker et al. |
| 5,919,234 A | 7/1999 | Lemperle et al. |
| 5,935,594 A | 8/1999 | Ringeisen et al. |
| 5,941,910 A | 8/1999 | Schindler et al. |
| 5,957,953 A | 9/1999 | DiPoto et al. |
| 5,968,043 A | 10/1999 | Ross, Jr. et al. |
| 5,976,142 A | 11/1999 | Chin |
| 5,977,431 A | 11/1999 | Knapp et al. |
| 5,980,252 A | 11/1999 | Samchukov et al. |
| 5,980,522 A | 11/1999 | Koros et al. |
| 5,990,382 A | 11/1999 | Fox |
| 5,964,767 A | 12/1999 | Tapia et al. |
| 5,997,520 A | 12/1999 | Ahr et al. |
| 6,018,094 A | 1/2000 | Fox |
| 6,019,764 A | 2/2000 | Bartee |
| 6,027,744 A | 2/2000 | Vacanti et al. |
| 6,030,218 A | 2/2000 | Robinson |
| 6,033,412 A | 3/2000 | Losken et al. |
| 6,037,384 A | 3/2000 | Kakizawa |
| 6,042,596 A | 3/2000 | Bonutti |
| 6,045,497 A | 4/2000 | Schweich et al. |
| 6,050,819 A | 4/2000 | Robinson |
| 6,077,076 A | 6/2000 | Comfort |
| 6,113,599 A | 9/2000 | Landsberger |
| 6,126,660 A | 10/2000 | Dietz |
| 6,127,597 A | 10/2000 | Beyar et al. |
| 6,206,930 B1 | 3/2001 | Burg et al. |
| 6,210,376 B1 | 4/2001 | Grayson |
| 6,214,012 B1 | 4/2001 | Karpman et al. |
| 6,217,323 B1 | 4/2001 | Liou |
| 6,224,599 B1 | 5/2001 | Baynham |
| 6,251,063 B1 | 6/2001 | Silverman et al. |
| 6,264,695 B1 | 7/2001 | Stoy |
| 6,270,346 B1 | 8/2001 | Grabenhofer et al. |
| 6,280,191 B1 | 8/2001 | Gordon |
| 6,293,947 B1 | 9/2001 | Buchbinder |
| 6,293,960 B1 | 9/2001 | Ken |
| 6,302,687 B1 | 10/2001 | King |
| 6,309,220 B1 | 10/2001 | Gittleman |
| 6,322,566 B1 | 11/2001 | Minoretti et al. |
| 6,328,765 B1 * | 12/2001 | Hardwick ............... A61L 27/58 623/23.72 |
| 6,358,266 B1 | 3/2002 | Bonutti |
| 6,402,518 B1 | 6/2002 | Ashman |
| 6,409,764 B1 | 6/2002 | White et al. |
| 6,506,214 B1 | 1/2003 | Gross |
| 6,616,698 B2 | 9/2003 | Scarborough |
| 6,679,914 B1 * | 1/2004 | Gabbay ............... A61L 27/3683 623/14.12 |
| 6,740,093 B2 | 4/2004 | Hochschuler et al. |
| 6,758,673 B2 | 7/2004 | Fromovich et al. |
| 7,153,306 B2 | 12/2006 | Ralph |
| 7,244,241 B2 | 7/2007 | Gross |
| 7,396,232 B2 | 7/2008 | Fromovich et al. |
| 7,510,397 B2 | 3/2009 | Hochman |
| 3,002,548 A1 | 8/2011 | Ho |
| 8,333,589 B2 | 12/2012 | Kfir |

(56) References Cited

U.S. PATENT DOCUMENTS

| | | | |
|---|---|---|---|
| 8,622,739 B2 | 1/2014 | Karmon | |
| 8,864,841 B2 | 10/2014 | Karmon | |
| 8,882,507 B2 | 11/2014 | Hertz | |
| 9,198,758 B2* | 12/2015 | McKay | A61F 2/2846 |
| 9,364,583 B2* | 6/2016 | McKay | A61L 27/3608 |
| 9,615,841 B2 | 4/2017 | Eder | |
| 9,655,994 B2* | 5/2017 | McKay | A61L 27/50 |
| 10,383,731 B2* | 8/2019 | Vickers | A61L 27/3608 |
| 10,390,827 B2* | 8/2019 | Hodgkinson | A61B 17/07292 |
| 11,311,383 B2 | 4/2022 | Vickers | |
| 2001/0012607 A1 | 8/2001 | Robinson | |
| 2002/0094951 A1 | 7/2002 | Horiuchi et al. | |
| 2002/0177102 A1 | 11/2002 | Martin et al. | |
| 2004/0059418 A1* | 3/2004 | McKay | A61L 31/14 |
| | | | 623/17.11 |
| 2004/0249471 A1* | 12/2004 | Bindseil | A61F 2/4455 |
| | | | 623/23.57 |
| 2005/0074437 A1 | 4/2005 | Horvath | |
| 2005/0192600 A1 | 9/2005 | Nicolo et al. | |
| 2005/0283255 A1* | 12/2005 | Geremakis | B29C 67/02 |
| | | | 606/76 |
| 2006/0084034 A1 | 4/2006 | Hochman | |
| 2006/0172255 A1 | 8/2006 | Hochman et al. | |
| 2006/0287732 A1 | 12/2006 | Pezeshkian | |
| 2007/0059827 A1 | 3/2007 | Horvath | |
| 2008/0044449 A1 | 2/2008 | McKay | |
| 2008/0319466 A1 | 12/2008 | Eder | |
| 2009/0181345 A1 | 7/2009 | Kfir | |
| 2010/0047733 A1 | 2/2010 | Nahlieli | |
| 2010/0049330 A1 | 2/2010 | Horvath | |
| 2010/0081111 A1 | 4/2010 | Better et al. | |
| 2010/0081112 A1 | 4/2010 | Better et al. | |
| 2010/0196841 A1 | 8/2010 | Nahlieli | |
| 2010/0203155 A1* | 8/2010 | Wei | A61F 2/4603 |
| | | | 606/86 R |
| 2010/0221681 A1 | 9/2010 | Hochman | |
| 2010/0255444 A1 | 10/2010 | Karmon | |
| 2011/0009978 A1 | 1/2011 | Horvath | |
| 2011/0039232 A1 | 2/2011 | Yu | |
| 2011/0270236 A1 | 11/2011 | Eder | |
| 2012/0171293 A1 | 7/2012 | Horvath | |
| 2013/0261634 A1 | 10/2013 | McKay | |
| 2013/0261671 A1 | 10/2013 | Horvath | |
| 2013/0261672 A1 | 10/2013 | Horvath | |
| 2013/0274819 A1 | 10/2013 | Horvath | |
| 2013/0280303 A1* | 10/2013 | Drapeau | A61K 35/32 |
| | | | 424/618 |
| 2014/0005794 A1 | 1/2014 | Horvath | |
| 2014/0038126 A1 | 2/2014 | Krastev | |
| 2014/0105988 A1 | 4/2014 | Horvath | |
| 2014/0106306 A1 | 4/2014 | Karmon | |
| 2014/0277570 A1* | 9/2014 | Behnam | A61L 27/54 |
| | | | 112/475.08 |
| 2017/0239050 A1* | 8/2017 | Vickers | A61L 27/3608 |

FOREIGN PATENT DOCUMENTS

| | | |
|---|---|---|
| DE | 19803628 A1 | 1/1999 |
| DE | 19907420 A1 | 9/2000 |
| DE | 10036027 A1 | 1/2002 |
| DE | 202006013643 U1 | 2/2008 |
| EP | 0107779 A1 | 5/1984 |
| EP | 0411767 A1 | 2/1991 |
| EP | 1159984 B1 | 12/2001 |
| EP | 1174094 A1 | 1/2002 |
| EP | 2062548 A3 | 5/2009 |
| EP | 3419563 A1 | 1/2019 |
| JP | 2004-518452 C1 | 6/2004 |
| JP | 2006192040 A | 7/2006 |
| JP | 2009-536070 A | 10/2009 |
| JP | 2012-509092 A | 4/2012 |
| JP | 2016010690 A | 1/2016 |
| KR | 1020110007794 | 1/2011 |
| KR | 20130006616 U | 11/2013 |
| WO | 1988/01517 | 3/1988 |
| WO | 1993/21858 | 11/1993 |
| WO | 1995/18638 | 7/1995 |
| WO | 1996/13221 | 5/1996 |
| WO | 1996/024310 | 8/1996 |
| WO | 99/00074 A1 | 1/1999 |
| WO | 1999/02214 | 1/1999 |
| WO | 200004940 | 2/2000 |
| WO | 2000/21455 | 4/2000 |
| WO | 2001091663 | 12/2001 |
| WO | 2006/096900 | 9/2006 |
| WO | 2007/129312 | 11/2007 |
| WO | 20110109817 A1 | 9/2011 |
| WO | 2011132871 A3 | 12/2011 |
| WO | 2014/000007 | 1/2014 |
| WO | 2017147117 A1 | 8/2017 |

OTHER PUBLICATIONS

Notice of Allowance in Japanese patent application No. 2019-520092 from Japanese Patent Office filed on Mar. 2, 2022.
Search report of priority document IL Application 248472 from Israeli Patent Office filed on May 7, 2017.
Communication under Rule 94(3) EPC in European patent application No. 17 791 750.7-1126 from European Patent Office filed on Jun. 15, 2020.
Summons to attend oral proceedings pursuant to Rule 115(1) EPC in European patent application No. 17 791 750.7-1122 from European Patent Office filed on May 31, 2021.
Communication under Rule 71(3) EPC in European patent application No. 17 791 750.7-1122 from European Patent Office filed on Mar. 12, 2022 (Intention to grant).
Notice before Acceptance of IL265931 from Israeli Patent Office filed on Mar. 1, 2022.
International Preliminary Report on Patentability Chapter filed on Apr. 16, 2019.
International Search Report filed on Apr. 19, 2018.
Written Opinion of the International Searching Authority filed on Apr. 19, 2018.

* cited by examiner

DEVICES FOR TISSUE AUGMENTATION

FIELD AND BACKGROUND OF THE INVENTION

The present invention relates mainly to devices for tissue augmentation and/or bone augmentation, methods of producing the devices and methods of using the devices. The devices can be used also for other treatments, for example directional release of medications and/or radiation.

Treatment of edentulous patients with dental implants called also osseointegrated fixtures, which are made mainly of titanium and/or zirconium, is a well known procedure in the art. The procedure includes installing a dental implant in the alveolar bone of an at least partially edentulous jaw. Usually several months are required for proper healing after implant installation. After healing, an abutment is installed on the (called also "coronal") portion of the dental implant. After several weeks, an artificial tooth may be mounted on the abutment and the procedure is complete. It is also possible in some cases to connect the abutment and/or the crown and/or the bridge and/or the denture and/or a dolder bar and/or any dental element to the dental implant much earlier and even in the same day.

Installation of implants requires sufficient alveolar bone, generally about 10 mm height and 7 mm width.

When a tooth is removed, the alveolar bone is gradually resorbed because of the absence of stimulus of ossification-inducing pressure from the teeth. As the resorption process advances, the size of the bone gets reduced, i.e. the bone on which the dental roots are positioned—the alveolar ridge start shrinking.

The absence of just one tooth can cause modifications throughout the dental arch and even prompt a possible softening (loss of insertion) which may cause the loss of other teeth. The absence of several teeth aggravates the problem. Bone loss may finally modify the patient's appearance and, depending on the loss, may make him incapable of receiving bridges, implants or even dentures.

It is then necessary to carry out several surgical operations to reconstruct the alveolar ridge of the maxilla (called also the maxillary bone) or mandible (called also mandibular bone or mandibular).

Although these methods of surgical reconstruction have been successfully performed, this type of operation has had drawbacks. Certain methods have involved opening the mucoperiosteal tissue called also periosteal tissue and/or gums and/or gingiva along the entire length of the atrophic alveolar ridge and then placing a bone graft material and a membrane on top of the graft and then suturing the delicate mucoperiosteal tissue back together to cover the membrane. The role of the membrane is to maintain the bone graft in its place and to prevent the mucoepithelium from growing into the graft and interfering with the process of bone regeneration. This surgical operation has drawbacks and usually only limited amount of bone regeneration can be achieved.

U.S. Pat. No. 7,749,267 to Karmon and U.S. Pat. No. 8,622,739 to Karmon, the entire disclosures of which are hereby incorporated by reference, disclose devices and methods to overcome some of these drawbacks. Karmon discloses a bag to be placed between the bone and the periosteal tissue, which can be filled with bone augmenting material. The bag can be perforated on the side facing the bone while the side facing the periosteal tissue can be made from a guided bone regeneration membrane and can have different properties than the perforated side. U.S. patent application No. 20150320463 to Karmon, the entire disclosure of which is hereby incorporated by reference, disclose devices and methods to treat fractures with bags that can be filled with bone augmenting material and can have a perforated side.

However preparation of such a bag is not trivial, especially when it is made from biological material like collagen or pericardium. The insertion of the bag inside a subperiosteal tunnel is not trivial either, especially in the posterior region of lower jaw, adjacent the mental nerve, which can be damaged during the insertion of the bag.

Therefore there is a need for better devices and methods for producing the bags and/or containers and methods that will allow safer insertion of the bags inside a subperiosteal tunnel, if a subperiosteal tunnel is used.

SUMMARY OF THE INVENTION

The present invention provides devices and methods to perform tissue regeneration. The following embodiments will focus on bone regeneration in the jaws, however similar devices can be used for other bones and/or tissues in the body. For example the bags can be used for regeneration of cartilage tissue in the knee or in other joints.

One of the inventions is a bag having one layer a membrane on side and two layers of a guided bone regeneration membrane on the opposite side. The side with one layer can be perforated with holes that allow bon tissue ingrowth. The bag can be completely bioresorbable. The side with the one layer can be made from other materials than the side with the two membranes. The side with the one layer can be made to be resorbed faster than the side with the two layers, however both sides can be fully and/or partially non-resorbable. The bag can be filled with a material that promotes bone growth. The bag can be placed in the jaw so the side with the one layer will be placed towards the bone and side with the two layers towards the gums. The side with the two layers can be such that it prevents soft tissue ingrowth inside the bag that will interfere with bone regeneration process.

Other objects and features of the present invention will become apparent in the following detailed description when taken in connection with the accompanying drawings which disclose several embodiments of the invention. It is to be understood that the drawings are designed for the purpose of illustration only and are not intended as a definition of the limits of the invention.

It is also to be understood that any combination of the embodiments described hereafter can be used although these combinations are not explicitly described. The number of possible combinations of different elements in different relations to each other and the number of options of using the devices is enormous. Therefore only several embodiments are described and illustrated.

The present invention provides a number of novel features, each of which is believed to be of patentable significance, and which can be combined in various combinations. A selection of the combinations will be described below, and other possible combinations will be clear to one ordinarily skilled in the art on the basis of this description. All features described below in the context of one exemplary embodiment of the present invention should be understood as being equally applicable to other embodiments except where the features are clearly incompatible or it is explicitly stated otherwise.

Thus, according to the teachings of the present invention there is provided a device for treating patients in need for tissue regeneration comprising:

A device for treating patients in need for tissue regeneration comprising:

a sheet, the sheet has a perforated region having several holes with diameter of more than 30 microns, the sheet has a first side region located at the right side of the perforated region, the sheet has a second side region located at the left side of the perforated region, the first side region has no pores or has pores such that the largest pore in the first side region has a diameter of up to 30 microns.

According to a further feature of the present invention, the second side region has no pores or has pores such that the largest pore in the second side region has a diameter of up to 30 microns.

According to a further feature of the present invention, the first and second side regions are placed above the perforated region forming a soft tissue blocking region above the perforated region, the soft tissue blocking region has no pores or has pores such that the largest pore in the soft tissue blocking region has a diameter of up to 30 microns.

According to a further feature of the present invention, the sheet has a middle region having several holes with diameter of more than 30 microns, the sheet has a first side region located at the right side of the middle region, the sheet has a second side region located at the left side of the middle region, the first and second side regions are placed above the perforated region forming a soft tissue blocking region above the perforated region, pores which are larger than 20 microns are absent from the soft tissue blocking region.

According to a further feature of the present invention, said first side region has a slot surrounding partially an area of said first side region to form a first retractable cover.

According to a further feature of the present invention, said second side region has a slot surrounding partially an area of said second side region to form a second retractable cover.

According to a further feature of the present invention said second retractable cover being larger than said first retractable cover, said second retractable cover overlaps and cover said first retractable cover in said soft-tissue blocking region to form a side opening in said soft-tissue blocking region when said first and second retractable covers are being retracted.

According to a further feature of the present invention, said first side region has a slot surrounding partially an area of said first side region to form a first retractable cover, said second side region has a slot surrounding partially an area of said second side region to form a second retractable cover, said second retractable cover being larger than said first retractable cover, said second retractable cover overlaps and cover said first retractable cover in said soft-tissue blocking region to form a side opening in said soft-tissue blocking region when said first and second retractable covers are being retracted.

According to a further feature of the present invention, said first retractable cover and said second retractable cover are being designed to be retracted to different directions.

According to a further feature of the present invention, said first retractable cover has a retractable cover fixating slot adjacent to said non-linear slot in said first side region, the length of said retractable cover fixating slot being compatible with the width of said second retractable cover.

According to a further feature of the present invention, the middle region has several holes with diameter of more than 30 microns to form a perforated region.

According to a further feature of the present invention, the middle region has more than 10 holes.

According to a further feature of the present invention, the middle region bio-dissipate faster than the first and second side regions.

According to a further feature of the present invention, the holes having diameter of more than 100 microns.

According to a further feature of the present invention, the holes having diameter of 500 microns-3000 microns.

According to a further feature of the present invention, the holes having diameter of 800 microns-2500 microns.

According to a further feature of the present invention, the holes occupy more than 70 percent of the perforated region.

According to a further feature of the present invention, the holes occupy more than 90 percent of the perforated region.

According to a further feature of the present invention, pores which are larger than 10 microns are absent from the soft tissue blocking region.

According to a further feature of the present invention, pores which are larger than 5 microns are absent from the soft tissue blocking region.

According to a further feature of the present invention, at least part the sheet is a guided regeneration membrane.

According to a further feature of the present invention, at least part the sheet is a pericardium membrane.

According to a further feature of the present invention, at least part the sheet is a collagen membrane.

According to a further feature of the present invention, at least part the sheet is a synthetic membrane.

According to a further feature of the present invention, the first side region is connected to the second side region.

According to a further feature of the present invention, the first side region is connected to the second side region by an adhesive layer located between the first side region and the second side region.

According to a further feature of the present invention, the first side region is connected to the second side region by sutures.

According to a further feature of the present invention, the first side region is connected to the second side region by heat and/or pressure.

According to a further feature of the present invention, the first side region is connected to the second side region in a non-continues manner so as to have non connected areas of the side regions between connected areas of the side regions.

According to a further feature of the present invention, the first side region has a slot and the second side region has a connecting extension, part of the connecting extension of the second side region having a width which is larger than the length of the slot in the first side region.

According to a further feature of the present invention, the part of the connecting extension of the second side region being inserted through the slot in the first side region.

According to a further feature of the present invention, the first side region has two adjacent slots and the second side region has a connecting extension, part of the connecting extension of the second side region having a width which is larger than the length of the slots in the first side region.

According to a further feature of the present invention, the part of the connecting extension of the second side region being inserted through the slots of the first side region.

According to a further feature of the present invention, the second side region has a slot and the first side region has a connecting extension, part of the connecting extension of the first side region having a width which is larger than the length of the slot in the second side region.

According to a further feature of the present invention, the part of the connecting extension of the first side region being inserted through the slot in the second side region.

According to a further feature of the present invention, one edge of the middle region being connected to the tissue blocking region to form a bag having a filling opening adjacent the opposite edge of the perforated region.

According to a further feature of the present invention, the middle region includes an edge closing extension, the edge closing extension being placed above at least part of the middle region to form a bag.

According to a further feature of the present invention, the middle region includes an edge closing extension, the edge closing extension being placed between the first side region and the second side region to form a bag.

According to a further feature of the present invention, a bone augmenting material is located between the middle region and the soft tissue blocking region.

According to a further feature of the present invention, a particulated bone augmenting material is located between the middle region and the soft tissue blocking region, the diameter of the particles of the bone augmenting material are larger than the diameter of the holes in the perforated region.

According to a further feature of the present invention, a particulated bone augmenting material is located between the middle region and the soft tissue blocking region, the diameter of the particles of the bone augmenting material are smaller than the diameter of the holes in the middle region and the particles are in a flowable material.

According to a further feature of the present invention, the edges of the middle region being connected to the tissue blocking region to form a bag, a bone augmenting material being inside the bag.

Thus, according to the teachings of the present invention there is provided a device for treating patients in need for tissue regeneration comprising:

a sheet, the sheet has a perforated region having several holes with diameter of more than 30 microns, the sheet has a first side region located at the right side of the perforated region, the sheet has a second side region located at the left side of the perforated region, the first and second side regions are placed above the perforated region forming a soft tissue blocking region above the perforated region, pores which are larger than 20 microns are absent from the soft tissue blocking region.

It must be clear that the sequence of placing the side regions and any other elements of the device as described above and hereafter can be changed, as long as a bag is formed. For example, the first side region can be placed over the perforated region and the second side region to be above the first side region. For example, the second side region can be placed over the perforated region and the first side region to be above the second side region According to a further feature of the present invention, said first side region has a slot surrounding partially an area of said first side region to form a first retractable cover.

According to a further feature of the present invention, said second side region has a slot surrounding partially an area of said second side region to form a second retractable cover.

According to a further feature of the present invention said second retractable cover being larger than said first retractable cover, said second retractable cover overlaps and cover said first retractable cover in said soft-tissue blocking region to form a side opening in said soft-tissue blocking region when said first and second retractable covers are being retracted.

According to a further feature of the present invention, said first side region has a slot surrounding partially an area of said first side region to form a first retractable cover, said second side region has a slot surrounding partially an area of said second side region to form a second retractable cover, said second retractable cover being larger than said first retractable cover, said second retractable cover overlaps and cover said first retractable cover in said soft-tissue blocking region to form a side opening in said soft-tissue blocking region when said first and second retractable covers are being retracted.

According to a further feature of the present invention, said first retractable cover and said second retractable cover are being designed to be retracted to different directions.

According to a further feature of the present invention, said first side region has a retractable cover fixating slot adjacent to said non-linear slot in said first sheet, the length of said retractable cover fixating slot being compatible with the width of said second retractable cover.

According to a further feature of the present invention, the perforated region has more than 10 holes.

According to a further feature of the present invention, the holes having diameter of more than 100 microns.

According to a further feature of the present invention, the holes having diameter of 500 microns-3000 microns.

According to a further feature of the present invention, the holes having diameter of 800 microns-2500 microns.

According to a further feature of the present invention, the holes occupy more than 70 percent of the perforated region.

According to a further feature of the present invention, the holes occupy more than 90 percent of the perforated region.

According to a further feature of the present invention, pores which are larger than 10 microns are absent from the soft tissue blocking region.

According to a further feature of the present invention, pores which are larger than 5 microns are absent from the soft tissue blocking region.

According to a further feature of the present invention, at least part the sheet is a guided regeneration membrane.

According to a further feature of the present invention, at least part the sheet is a pericardium membrane.

According to a further feature of the present invention, at least part the sheet is a collagen membrane.

According to a further feature of the present invention, at least part the sheet is a synthetic membrane.

According to a further feature of the present invention, the first side region is connected to the second side region.

According to a further feature of the present invention, the first side region is connected to the second side region by an adhesive layer located between the first side region and the second side region.

According to a further feature of the present invention, the first side region is connected to the second side region by sutures.

According to a further feature of the present invention, the first side region is connected to the second side region by heat and/or pressure.

According to a further feature of the present invention, the first side region is connected to the second side region in a non-continues manner so as to have non connected areas of the side regions between connected areas of the side regions.

According to a further feature of the present invention, the first side region has a slot and the second side region has a connecting extension, part of the connecting extension of the second side region having a width which is larger than the length of the slot in the first side region.

According to a further feature of the present invention, the part of the connecting extension of the second side region being inserted through the slot in the first side region.

According to a further feature of the present invention, the first side region has two adjacent slots and the second side region has a connecting extension, part of the connecting extension of the second side region having a width which is larger than the length of the slots in the first side region.

According to a further feature of the present invention, the part of the connecting extension of the second side region being inserted through the slots of the first side region.

According to a further feature of the present invention, the second side region has a slot and the first side region has a connecting extension, part of the connecting extension of the first side region having a width which is larger than the length of the slot in the second side region.

According to a further feature of the present invention, the part of the connecting extension of the first side region being inserted through the slot in the second side region.

According to a further feature of the present invention, one edge of the perforated region being connected to the tissue blocking region to form a bag having a filling opening adjacent the opposite edge of the perforated region.

According to a further feature of the present invention, the perforated region includes an edge closing extension, the edge closing extension being placed above at least part of the holes in the perforated region to form a bag.

According to a further feature of the present invention, the perforated region includes an edge closing extension, the edge closing extension being placed between the first side region and the second side region to form a bag.

According to a further feature of the present invention, a bone augmenting material is located between the perforated region and the soft tissue blocking region.

According to a further feature of the present invention, a particulated bone augmenting material is located between the perforated region and the soft tissue blocking region, the diameter of the particles of the bone augmenting material are larger than the diameter of the holes in the perforated region.

According to a further feature of the present invention, a particulated bone augmenting material is located between the perforated region and the soft tissue blocking region, the diameter of the particles of the bone augmenting material are smaller than the diameter of the holes in the perforated region and the particles are in a flowable material.

According to a further feature of the present invention, the edges of the perforated region being connected to the tissue blocking region to form a bag, a bone augmenting material being inside the bag.

Thus, according to the teachings of the present invention there is provided a device for treating patients in need for tissue regeneration comprising:
a tube, a first aspect of the tube has a perforated region having several holes with diameter of more than 30 microns, a second aspect of the tube has a soft tissue blocking region located above the perforated region, the soft tissue blocking region has a first sheet and a second sheet, the second sheet located above the first sheet, pores which are larger than 20 microns are absent from the soft tissue blocking region.

According to a further feature of the present invention, said first sheet has a slot surrounding partially an area of said first sheet to form a first retractable cover.

According to a further feature of the present invention, said second sheet has a slot surrounding partially an area of said second sheet to form a second retractable cover.

According to a further feature of the present invention said second retractable cover being larger than said first retractable cover, said second retractable cover overlaps and cover said first retractable cover in said soft-tissue blocking region to form a side opening in said soft-tissue blocking region when said first and second retractable covers are being retracted.

According to a further feature of the present invention, said first sheet has a slot surrounding partially an area of said first sheet to form a first retractable cover, said second sheet has a slot surrounding partially an area of said second sheet to form a second retractable cover, said second retractable cover being larger than said first retractable cover, said second retractable cover overlaps and cover said first retractable cover in said soft-tissue blocking region to form a side opening in said soft-tissue blocking region when said first and second retractable covers are being retracted.

According to a further feature of the present invention, said first retractable cover and said second retractable cover are being designed to be retracted to different directions.

According to a further feature of the present invention, said first retractable cover has a retractable cover fixating slot adjacent to said non-linear slot in said first sheet, the length of said retractable cover fixating slot being compatible with the width of said second retractable cover.

According to a further feature of the present invention, the perforated region has more than 10 holes.

According to a further feature of the present invention, the holes having diameter of more than 100 microns.

According to a further feature of the present invention, the holes having diameter of 500 microns-3000 microns.

According to a further feature of the present invention, the holes having diameter of 800 microns-2500 microns.

According to a further feature of the present invention, the holes occupy more than 70 percent of the perforated region.

According to a further feature of the present invention, the holes occupy more than 90 percent of the perforated region.

According to a further feature of the present invention, pores which are larger than 10 microns are absent from the soft tissue blocking region.

According to a further feature of the present invention, pores which are larger than 5 microns are absent from the soft tissue blocking region.

According to a further feature of the present invention, at least one of said sheets is a guided regeneration membrane.

According to a further feature of the present invention, at least one of said sheets is a pericardium membrane.

According to a further feature of the present invention, at least one of said sheets is a collagen membrane.

According to a further feature of the present invention, at least one of said sheets is a synthetic membrane.

According to a further feature of the present invention, the first sheet region is connected to the second sheet.

According to a further feature of the present invention, the first sheet is connected to the second sheet by an adhesive layer located between the first sheet and the second sheet.

According to a further feature of the present invention, the first sheet is connected to the second sheet by sutures.

According to a further feature of the present invention, the first sheet is connected to the second sheet by heat and/or pressure.

According to a further feature of the present invention, the first sheet is connected to the second sheet in a non-continues manner so as to have non connected areas of the sheets between connected areas of the sheets.

According to a further feature of the present invention, one edge of the perforated region being connected to the tissue blocking region to form a bag having a filling opening adjacent the opposite edge of the perforated region.

According to a further feature of the present invention, the perforated region includes an edge closing extension, the edge closing extension being placed above at least part of the holes in the perforated region to form a bag.

According to a further feature of the present invention, the perforated region includes an edge closing extension, the edge closing extension being placed between the first sheet and the second sheet to form a bag.

According to a further feature of the present invention, a bone augmenting material is located between the perforated region and the soft tissue blocking region.

According to a further feature of the present invention, a particulated bone augmenting material is located between the perforated region and the soft tissue blocking region, the diameter of the particles of the bone augmenting material are larger than the diameter of the holes in the perforated region.

According to a further feature of the present invention, a particulated bone augmenting material is located between the perforated region and the soft tissue blocking region, the diameter of the particles of the bone augmenting material are smaller than the diameter of the holes in the perforated region and the particles are in a flowable material.

According to a further feature of the present invention, the edges of the perforated region being connected to the soft tissue blocking region to form a bag, a bone augmenting material being inside the bag.

Thus, according to the teachings of the present invention there is provided a device for treating patients in need for tissue regeneration comprising:

a bag, a first aspect of the bag has a perforated region having several holes with diameter of more than 30 microns, a second aspect of the bag has a soft tissue blocking region located above the perforated region, the soft tissue blocking region has a first sheet and a second sheet, the second sheet located above the first sheet, pores which are larger than 20 microns are absent from the soft tissue blocking region.

According to a further feature of the present invention, said first sheet has a slot surrounding partially an area of said first sheet to form a first retractable cover.

According to a further feature of the present invention, said second sheet has a slot surrounding partially an area of said second sheet to form a second retractable cover.

According to a further feature of the present invention said second retractable cover being larger than said first retractable cover, said second retractable cover overlaps and cover said first retractable cover in said soft-tissue blocking region to form a side opening in said soft-tissue blocking region when said first and second retractable covers are being retracted.

According to a further feature of the present invention, said first sheet has a slot surrounding partially an area of said first sheet to form a first retractable cover, said second sheet has a slot surrounding partially an area of said second sheet to form a second retractable cover, said second retractable cover being larger than said first retractable cover, said second retractable cover overlaps and cover said first retractable cover in said soft-tissue blocking region to form a side opening in said soft-tissue blocking region when said first and second retractable covers are being retracted.

According to a further feature of the present invention, said first retractable cover and said second retractable cover are being designed to be retracted to different directions.

According to a further feature of the present invention, said first retractable cover has a retractable cover fixating slot adjacent to said non-linear slot in said first sheet, the length of said retractable cover fixating slot being compatible with the width of said second retractable cover.

According to a further feature of the present invention, the perforated region has more than 10 holes.

According to a further feature of the present invention, the holes having diameter of more than 100 microns.

According to a further feature of the present invention, the holes having diameter of 500 microns-3000 microns.

According to a further feature of the present invention, the holes having diameter of 800 microns-2500 microns.

According to a further feature of the present invention, the holes occupy more than 70 percent of the perforated region.

According to a further feature of the present invention, the holes occupy more than 90 percent of the perforated region.

According to a further feature of the present invention, pores which are larger than 10 microns are absent from the soft tissue blocking region.

According to a further feature of the present invention, pores which are larger than 5 microns are absent from the soft tissue blocking region.

According to a further feature of the present invention, at least one of said sheets is a guided regeneration membrane.

According to a further feature of the present invention, at least one of said sheets is a pericardium membrane.

According to a further feature of the present invention, at least one of said sheets is a collagen membrane.

According to a further feature of the present invention, at least one of said sheets is a synthetic membrane.

According to a further feature of the present invention, the first sheet is connected to the second sheet.

According to a further feature of the present invention, the first sheet is connected to the second sheet by an adhesive layer located between the first sheet and the second sheet.

According to a further feature of the present invention, the first sheet is connected to the second sheet by sutures.

According to a further feature of the present invention, the first sheet is connected to the second sheet by heat and/or pressure.

According to a further feature of the present invention, the first sheet is connected to the second sheet in a non-continues manner so as to have non connected areas of the sheets between connected areas of the sheets.

According to a further feature of the present invention, the bag having a filling opening adjacent one edge of the perforated region.

According to a further feature of the present invention, the perforated region includes an edge closing extension, the edge closing extension being placed above at least part of the holes in the perforated region to close the bag.

According to a further feature of the present invention, the perforated region includes an edge closing extension, the edge closing extension being placed between the first sheet and the second sheet to close the bag.

According to a further feature of the present invention, a bone augmenting material is located between the perforated region and the soft tissue blocking region.

According to a further feature of the present invention, a particulated bone augmenting material is located between the perforated region and the soft tissue blocking region, the diameter of the particles of the bone augmenting material are larger than the diameter of the holes in the perforated region.

According to a further feature of the present invention, a particulated bone augmenting material is located between the perforated region and the soft tissue blocking region, the diameter of the particles of the bone augmenting material are smaller than the diameter of the holes in the perforated region and the particles are in a flowable material.

According to a further feature of the present invention, an edge of the perforated region being connected to the soft tissue blocking region to close the bag, a bone augmenting material being inside the bag.

Thus, according to the teachings of the present invention there is provided a method for preparing a device for treating patients in need for tissue regeneration comprising:

a. perforating a region of a sheet with several holes having a diameter of more than 30 microns to form a perforated region;

b. folding a first side region of the sheet located on the right side of the perforated region above the perforated region;

c. folding a second side region of the sheet located on the left side of the perforated region above the first side region so the first and second side regions form a soft tissue blocking region, pores which are larger than 20 microns are absent from the soft tissue blocking region.

According to a further feature of the present invention, said first side region has a slot surrounding partially an area of said first side region to form a first retractable cover.

According to a further feature of the present invention, said second side region has a slot surrounding partially an area of said second side region to form a second retractable cover.

According to a further feature of the present invention said second retractable cover being larger than said first retractable cover, said second retractable cover overlaps and cover said first retractable cover in said soft-tissue blocking region to form a side opening in said soft-tissue blocking region when said first and second retractable covers are being retracted.

According to a further feature of the present invention, said first side region has a slot surrounding partially an area of said first side region to form a first retractable cover, said second side region has a slot surrounding partially an area of said second side region to form a second retractable cover, said second retractable cover being larger than said first retractable cover, said second retractable cover overlaps and cover said first retractable cover in said soft-tissue blocking region to form a side opening in said soft-tissue blocking region when said first and second retractable covers are being retracted.

According to a further feature of the present invention, said first retractable cover and said second retractable cover are being designed to be retracted to different directions.

According to a further feature of the present invention, said first side region has a retractable cover fixating slot adjacent to said non-linear slot in said first sheet, the length of said retractable cover fixating slot being compatible with the width of said second retractable cover.

According to a further feature of the present invention, the edges of the perforated region being connected to the soft tissue blocking region to form a bag, a bone augmenting material being inside the bag.

According to a further feature of the present invention, the perforated region has more than 10 holes.

According to a further feature of the present invention, the holes having diameter of more than 100 microns.

According to a further feature of the present invention, the holes having diameter of 500 microns-3000 microns.

According to a further feature of the present invention, the holes having diameter of 800 microns-2500 microns.

According to a further feature of the present invention, the holes occupy more than 70 percent of the perforated region.

According to a further feature of the present invention, the holes occupy more than 90 percent of the perforated region.

According to a further feature of the present invention, pores which are larger than 10 microns are absent from the soft tissue blocking region.

According to a further feature of the present invention, pores which are larger than 5 microns are absent from the soft tissue blocking region.

According to a further feature of the present invention, at least part of the sheet is a guided regeneration membrane.

According to a further feature of the present invention, at least part of the sheet is a pericardium membrane.

According to a further feature of the present invention, at least part of the sheet is a collagen membrane.

According to a further feature of the present invention, at least part of the sheet is a synthetic membrane.

According to a further feature of the present invention, the first side region is connected to the second side region.

According to a further feature of the present invention, the first side region is connected to the second side region by an adhesive layer located between the first side region and the second side region.

According to a further feature of the present invention, the first side region is connected to the second side region by sutures.

According to a further feature of the present invention, the first side region is connected to the second side region by heat and/or pressure.

According to a further feature of the present invention, the first side region is connected to the second side region in a non-continues manner so as to have non connected areas of the side regions between connected areas of the side regions.

According to a further feature of the present invention, the first side region has a slot and the second side region has a connecting extension, part of the connecting extension of the second side region having a width which is larger than the length of the slot in the first side region.

According to a further feature of the present invention, the part of the connecting extension of the second side region being inserted through the slot in the first side region.

According to a further feature of the present invention, the first side region has two adjacent slots and the second side region has a connecting extension, part of the connecting extension of the second side region having a width which is larger than the length of the slots in the first side region.

According to a further feature of the present invention, the part of the connecting extension of the second side region being inserted through the slots of the first side region.

According to a further feature of the present invention, the second side region has a slot and the first side region has a connecting extension, part of the connecting extension of the first side region having a width which is larger than the length of the slot in the second side region.

According to a further feature of the present invention, the part of the connecting extension of the first side region being inserted through the slot in the second side region.

According to a further feature of the present invention, one edge of the perforated region being connected to the soft tissue blocking region to form a bag having a filling opening adjacent the opposite edge of the perforated region.

According to a further feature of the present invention, the perforated region includes an edge closing extension, the edge closing extension being placed above at least part of the holes in the perforated region to form a bag.

According to a further feature of the present invention, the perforated region includes an edge closing extension, the edge closing extension being placed between the first side region and the second side region to form a bag.

According to a further feature of the present invention, a bone augmenting material is located between the perforated region and the soft tissue blocking region.

According to a further feature of the present invention, a particulated bone augmenting material is located between the perforated region and the soft tissue blocking region, the diameter of the particles of the bone augmenting material are larger than the diameter of the holes in the perforated region.

According to a further feature of the present invention, a particulated bone augmenting material is located between the perforated region and the soft tissue blocking region, the diameter of the particles of the bone augmenting material are smaller than the diameter of the holes in the perforated region and the particles are in a flowable material.

According to a further feature of the present invention, the edges of the perforated region being connected to the tissue blocking region to form a bag, a bone augmenting material being inside the bag.

Thus, according to the teachings of the present invention there is provided a method for treating patients in need for tissue regeneration in the lower jaw comprising:

a. detaching the lingual periosteal tissue from a lingual surface of the lower jaw bone to form a lingual opening between the lingual periosteal tissue and the lingual surface of the lower jaw bone;

b. forming a subperiosteal tunnel through the lingual opening, the subperiosteal tunnel extends from the lingual opening along a segment of the lower jaw bone and a segment of a periosteal tissue;

c. inserting through the lingual opening a bag inside the subperiosteal tunnel, the bag has a perforated region having holes which are larger than 30 microns, the bag has a soft tissue blocking region in which holes which are larger than 20 microns are absent, the bag contain a bone augmenting material, the perforated region of the bag being placed towards at least part of the segment of the lower jaw bone, the soft tissue blocking region being placed towards at least part of the segment of the periosteal tissue.

d. closing the lingual opening and leaving the bag adjacent the segment of the lower jaw bone for at least several days to allow bone tissue ingrowth through the holes inside the bag.

According to a further feature of the present invention, the soft tissue blocking region has a at least one retractable cover that when being retracted forms an opening to allow filling of the bag.

According to a further feature of the present invention, the segment of the periosteal tissue being located distally to the lingual opening.

According to a further feature of the present invention, the segment of the periosteal tissue being located mesially to the lingual opening.

According to a further feature of the present invention, an additional bone augmenting being inserted inside the subperiosteal tunnel adjacent to the bag.

According to a further feature of the present invention, an additional bone augmenting being inserted inside the subperiosteal tunnel between the bag and the segment of the lower jaw.

According to a further feature of the present invention, an opening to the subperiosteal tunnel is being formed also in the buccal aspect of the lower.

According to a further feature of the present invention, the lingual opening being enlarged to reach the buccal aspect of the lower jaw.

According to a further feature of the present invention, the subperiosteal tunnel extends along an occlusal aspect of the segment of the lower jaw.

According to a further feature of the present invention, the subperiosteal tunnel extends along a buccal aspect of the segment of the lower jaw.

According to a further feature of the present invention, the bag being placed along a buccal aspect of the segment of the lower jaw.

According to a further feature of the present invention, the bag being placed along an occlusal aspect of the segment of the lower jaw.

According to a further feature of the present invention, the bag being placed along a lingual aspect of the segment of the lower jaw.

According to a further feature of the present invention, the bag being fixated to the lower jaw using a bone tack.

According to a further feature of the present invention, the bag being fixated to the lower jaw using a screw.

According to a further feature of the present invention, the bag being fixated to the lower jaw using a glue.

According to a further feature of the present invention, the bag being fixated to the periosteal tissue using a suture.

According to a further feature of the present invention, the bag being fixated to the periosteal tissue using a glue.

According to a further feature of the present invention, the bag being filled using a syringe having the bone augmenting material.

According to a further feature of the present invention, the perforated region has more than 10 holes.

According to a further feature of the present invention, the holes having diameter of more than 100 microns.

According to a further feature of the present invention, the holes having diameter of 500 microns-3000 microns.

According to a further feature of the present invention, the holes having diameter of 800 microns-2500 microns.

According to a further feature of the present invention, the holes occupy more than 70 percent of the perforated region.

According to a further feature of the present invention, the holes occupy more than 90 percent of the perforated region.

According to a further feature of the present invention, holes which are larger than 10 microns are absent from the soft tissue blocking region.

According to a further feature of the present invention, holes which are larger than 5 microns are absent from the soft tissue blocking region.

According to a further feature of the present invention, at least part of the soft tissue blocking region is made from a guided regeneration membrane.

According to a further feature of the present invention, at least part of the soft tissue blocking region is made from pericardium membrane.

According to a further feature of the present invention, at least part the soft tissue blocking region is made from collagen membrane.

According to a further feature of the present invention, at least part the soft tissue blocking region is made from synthetic membrane.

According to a further feature of the present invention, at least part the soft tissue blocking region has a first sheet and a second sheet above the first sheet.

According to a further feature of the present invention, the first sheet is connected to the second sheet by an adhesive layer located between the first sheet and the second sheet.

According to a further feature of the present invention, the first sheet is connected to the second sheet by sutures.

According to a further feature of the present invention, the first sheet is connected to the second sheet by heat and/or pressure.

According to a further feature of the present invention, the first sheet is connected to the second sheet in a non-continues manner so as to have non connected areas of the sheets between connected areas of the sheets.

According to a further feature of the present invention, the first sheet has a slot and the second sheet has a connecting extension, part of the connecting extension of the second sheet having a width which is larger than the length of the slot in the first sheet.

According to a further feature of the present invention, the part of the connecting extension of the second sheet being inserted through the slot in the first sheet.

According to a further feature of the present invention, the first sheet has two adjacent slots and the second sheet has a connecting extension, part of the connecting extension of the second sheet having a width which is larger than the length of the slots in the first sheet.

According to a further feature of the present invention, the part of the connecting extension of the second sheet being inserted through the slots of the first sheet.

According to a further feature of the present invention, the second sheet has a slot and the first sheet has a connecting extension, part of the connecting extension of the first sheet having a width which is larger than the length of the slot in the second sheet.

According to a further feature of the present invention, the part of the connecting extension of the first sheet being inserted through the slot in the second sheet.

According to a further feature of the present invention, one edge of the perforated region being connected to the soft tissue blocking region to form the bag having a filling opening adjacent the opposite edge of the perforated region.

According to a further feature of the present invention, the perforated region includes an edge closing extension, the edge closing extension being placed above at least part of the holes in the perforated region to form the bag.

According to a further feature of the present invention, the perforated region includes an edge closing extension, the edge closing extension being placed between the first sheet and the second sheet to form the bag.

According to a further feature of the present invention, the bone augmenting material includes a particulated bone augmenting material, the diameter of the particles of the bone augmenting material are larger than the diameter of the holes in the perforated region.

According to a further feature of the present invention, the bone augmenting material includes a particulated bone augmenting material, the diameter of the particles of the bone augmenting material are smaller than the diameter of the holes in the perforated region and the particles are in a flowable material.

According to a further feature of the present invention, the edges of the perforated region being connected to the tissue blocking region to form the bag.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
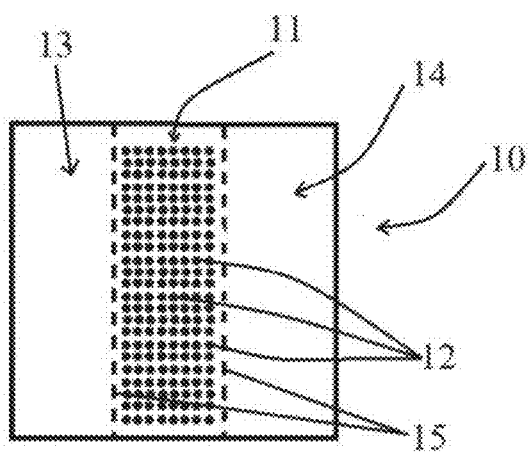
FIG. 1 is a perspective view illustrating an embodiment of a sheet having a perforated region.

Before turning to the features of the present invention in more detail, it will be useful to clarify certain terminology as will be used herein in the description and claims. Specifically, it should be noted that the present invention is useful in a wide range of applications in which living tissue is to be regenerated or treated. The term "living tissue" is used herein to refer to any living tissue including, but not limited to bone, an organ, tube, vessel, cavity, bone cavity or membrane, and interfaces between any two or more of the above. Where used within a single type of tissue, the typical application of the present invention is for regenerating the tissue inside the tissue. When used at a tissue interface, the invention is typically used to separate between tissues and/or treating only one tissue.

It is noted that a large number of different types of materials are known which may be inserted within the body during a surgical procedure and which later dissipate, thereby avoiding the need for a separate surgical procedure for their removal. Such materials are properly referred to, depending upon the mechanism by which the material dissipates, as "resobable", "bioresorbable", "absorbable", "bioabsorbable", "degradable" or "biodegradable". Despite the differences between these different classes of materials, the aforementioned terminology is widely used interchangeably by medical professionals. Accordingly, and for conciseness of presentation, only one of these terms will generally be used in the following description, without implying the exclusion of the other classes of materials. Additionally, the phrase "bio-dissipative material" is used herein in the description and claims to refer generically to any and all materials which dissipate without requiring surgical removal, independent of which mechanisms such as dissolution, degradation, absorption and excretion take place. The actual choice of which type of materials to use may readily be made by one ordinarily skilled in the art.

The bone can be regenerated by several biological mechanisms: Osteogenesis in which the bone augmenting material includes bone forming cells; Osteoinduction in which the bone augmenting material includes materials that induce cells to form bone or to differentiate to become bone forming cells; Osteoconduction in which the bone augmenting material provides a scaffold for bone forming cells; or Osteopromotion in which encouraging the biologic or mechanical environment of bone regeneration. The bone augmenting material can be an autograft, an allograft, a xenograft, an alloplast, a cytokine, a hormone, a growth factor, a physiologically acceptable drug, a biological modifier, a protein (for example Bone Morphogenetic Protein (like BMP-2, BMP-7)), an antigen, a cell chemotaxis stimulator material, a material inducing osteogenesis, an osteoinduction material, an osteoconduction material, a bioactive material, a bioresorbable material, a bioabsorbable material, a bio-dissipative material and any combination thereof. The bone augmenting material can include materials that occupy a space in the body for at least several weeks. These materials preferably encourage the tissue to grow inside the space occupied by the material. This is the principle function of most bone augmenting materials available on the market. The bone augmenting material can be entirely bio-dissipative. The bone augmenting material can be available in the market like hydroxyapatite, bovine mineral (i.e. Bio-Oss available from Geistlich, Switzerland), materials from other species, for example, equine origin materials, materials combining mineral and collagen (i.e. OX granules available from Bioteck SPA, Italy), demineralized frizzed dried bone allograft, synthetic materials like PLA or suspension of mineral particles (from various origins) in a liquid medium. The bone augmenting material can be also fully or partially not bio-dissipative, for example crystal hydroxyapatite. The bone augmenting material can include therapeutic materials.

The bone augmenting material can be a biocompatible filing material that sets and becomes rigid inside the tissue. The biocompatible filling material can be a bio-dissipative material that contains materials assisting in the process of bone healing like bone cements, for example Skeletal Repair System (SRS) from Norian company, Healos from Orquest company, OsteoGenics and Orthovita's Orthocomp from Howmedical Leibinger company.

Most bone augmenting materials are available as particles in the size of 200-2000 microns. To allow easy insertion, preferably the particles are mixed with a solution like saline, blood or biocompatible gels like cellulose, glycerol and/or hydrogel. The bone augmenting material can be high viscous gel like Dinagraft which is gelatinous allograft bone augmenting material and/or with bone cements calcium sulfate and/or calcium carbonate. Additionally, the phrase "augmenting material" is used herein in the description and claims to refer generically to any and all these materials and mechanisms and in all mediums and/or gels in which these materials are mixed with. The actual choice of which type of materials and/or combination of materials to use may readily be made by one ordinarily skilled in the art.

Along the description sometimes the device is called "bag" and sometimes "container". Both terms refer to a device that can contain bone augmenting material. The "container" or "bag" can be also a pouch or cloth like pouch in all the embodiments.

The term "anterior" means more towards the front and close to the lips. The term "posterior" mean more towards the back and close to the throat. The term "buccal" means the side towards the cheeks and lips. The term "lingual" means the side towards the tongue. The term "mesial" inside the mouth means in dentistry towards the location of central teeth along the dental arch. The term "distal" inside the mouth means in dentistry towards the location of posterior teeth along the dental arch.

The term membrane means a sheet of material that can be made from variable materials in variable shapes and any combination of materials. The membrane preferably can be made from biocompatible materials. The membrane can be partially or completely bio-dissipative or can be completely non resorbable. The membrane can be made from artificial materials, for example polyglycolic acid (PGA) mesh, a high-molecular-weight linear polymer made by the ring opening polymerization of the purified glycolide monomer, e.g. polyglactin 910, i.e. polyglycolide co-galactide or/and PDS (another absorbable suture material) and/or cellulose which are bio-disipative or can be made from PTFE and/or ePTFE and/or Teflon which are not resorbable. The membrane can be made from autograft, allograft, xenograft and any combination thereof. For example the membrane can be made from collagen and/or cross-linked collagen. The membrane can be made from pericardium, peritoneum, vessels and other tissues and/or biological membranes. The membrane can have different thickness at different regions of the membrane. The membrane can have different stiffness and/or flexibility at different regions of the membrane. The membrane can have more than one layer and each layer can have different properties and/or can be made from different materials. The membrane can include a guided tissue regeneration membrane and/or guided bone regeneration membrane. Guided bone regeneration (GBR) membranes are used in dental implant dentistry to regenerate bone. The GBR membranes prevent the epithelial and connective tissue to penetrate the bone defect and interfere with the bone regeneration process. The membrane can be any combination of the above.

When the bag is inserted inside a subperiosteal tunnel, there is an advantage to using a tear resistant membrane like a pericardium membrane, for example Jason membrane from Botiss (Germany) or like compressed collagen, for example Bio-Gide compress from Geistlich (Switzerland).

Along the description sometimes the device and/or part of it is called "sheet" and sometimes "membrane". Both terms refer to a device and/or part of the device which can be used to form a bag. The sheet or membrane is usually flexible like a cloth or a fabric. The sheet or membrane can be cloth like ready to use or might requires hydration to become less stiff and more flexible like a fabric.

Along the description holes and/or perforations are mentioned having different optional diameters. The use of the term "diameter" doesn't necessarily imply that the shape of the holes is round. The holes can have various shapes like ellipse and/or polygonal shapes for example square or hexagon and can have a non-regular or non-defined shape.

The term mucoperiosteal tissue in the jaws can mean also gums and/or gingiva.

Finally with respect to terminology, reference will be made to a flowable material that can be used to fill the containers and/or bags of the present invention. It should be noted that this flowable material may assume a wide range of compositions and consistencies, so long as the filling material may be inserted into the container. Thus, possible consistencies for the filling material include, but are not limited to, consistencies described as watery, viscous, gelatinous, moldable, waxen, particulate, and suspensions or mixtures combining any of the above. The filling material can be also any kind of a bone augmenting material described above, which can be a flowable material. The bone augmenting material can be a suspension of particles is a solution like saline. The bone augmenting material can be particles inside gel. The particles can be from any type of bone augmenting material motioned above and the gel can be from any type of bone augmenting material mentioned above. The gel can include collagen and/or any material encouraging bone formation.

Turning now in detail to the drawings, which depict the presently preferred embodiments of the invention for the purpose of illustrating the practice thereof and not by way of limitation of the scope of the invention, and in which like reference characters refer to corresponding elements throughout the several views.

Figure 2:
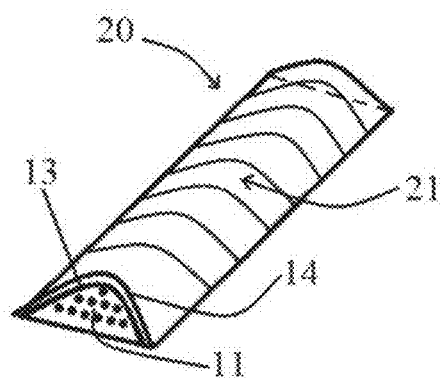
FIG. 2 is a perspective view illustrating an embodiment of a tube formed after folding and/or rolling the sheet of FIG. 1.

FIG. 1, illustrates a sheet of a membrane 10 (hereafter called sheet and/or membrane) having a middle region 11 (between the dotted lines in FIG. 1) which can be perforated with several holes 12 and two side regions 13, 14 on each side of the middle region. The middle region 11 doesn't have to be at the middle of the sheet. The side regions 13, 14 can be not perforated. The side regions can include perforations with a diameter up to 5 microns and/or up to 10 microns and/or up to 15 microns and/or up to 20 microns and/or up to 25 microns and/or up to 30 microns so the diameter of largest hole in the side regions 13, 14 can be 5 microns or 10 microns or 15 microns or 20 microns or 25 microns or 30 microns. The side regions 13, 14 and the middle region 11 can have several types of holes with different dimensions and different shapes. The sheet 10 can be folded and/or rolled so a first side region 13 can be placed over the middle region 11 and a second side region 14 can be placed over the first side region 13. This folding and/or rolling of the sheet membrane 10 can create a tube like structure 20 as illustrated in FIG. 2. The tube like structure 20 can have a middle perforated region 11 on one side of the tube 20 and two layers of membrane 13, 14 (the first and second side regions) on the other side of the tube 20, forming a soft tissue blocking region 21 of the tube 20.

The folding can be along the folding lines 15. The folding can be assisted by placing a stick having a width like the width of the middle region, between the folding lines 15. The stick can be place on the middle region 11 and the side regions 13, 14 folded on the stick. The folding line 15 can include perforations and/or small slots having length of 0.5-3 mm or 1-2 mm or more than 3 mm. The folding lines 15 can include places having thinner width, like an imprint and/or an embossing in the membrane 11 along the folding lines 15 having length of 0.5-3 mm or 1-2 mm or more than 3 mm. These slots or embossing will enable easy folding of the membrane 11 along the folding lines 15.

The second side region 14 can be connected to the first side region 13 and/or to the middle region 11 so the tube 20 keeps its tube structure and to prevent unfolding of the sheet membrane 10. The connection between the regions can be for example by suturing and/or gluing with biocompatible sutures/glues. The connection between the regions can be also by pressure and/or heat.

The tube doesn't have to be oval and can have any other morphology.

The glue mentioned above and later can be a polymer and/or hydrogel which polymerize under radiation during the sterilization process as described in international application No. WO 2015/107502 to Bioteck S.P.A., the entire disclosure of which is hereby incorporated by reference.

The glue can be a flexible glue to keep the bag flexible so it will easily adapt to the bone morphology. The glue can be placed with intervals and/or only in several points so as to keep the flexibility of the bag.

Figure 3:
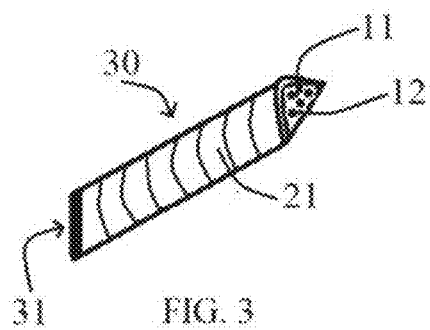
FIG. 3 is a perspective view illustrating an embodiment of a bag formed after closing one edge of the tube of FIG. 2 while the other edge is open.

The tube 20 can be closed at one edge 31 of the tube to form a container 30 as illustrated in FIG. 3. The closing can be for example by suturing and/or gluing with biocompatible sutures/glues. The closing of the tube edge 31 can be also by pressure and/or heat. It is possible to fold and/or roll the tube edge 31 before closing or to close it without folding and/or rolling.

The device can be marketed to the surgeon as a sheet membrane 10, like the membrane illustrated in FIG. 1 with the middle region that can be perforated and the side regions 13, 14, and the surgeon will fold and/or roll and connect the side regions 13, 14 to form the tube 20 as illustrated in FIG. 2. Then the surgeon can close one edge 31 of the tube 20 to form the container 30 like the container illustrated in FIG. 3.

The device can be marketed to the surgeon as a tube 20, like the tube illustrated in FIG. 2. Then the surgeon can close one edge 31 to form the container 30 like the container illustrated in FIG. 3.

The device can be marketed to the surgeon already as a container 30, like the container illustrated in FIG. 3.

The container 30 can be filled with bone augmenting material. It can be filled with several bone augmenting materials, having different properties and with any combination of bone augmenting materials and/or any combination of a bone augmenting material and other materials like for example carriers, gels, polymers and hydrogels. The container 30 can be filled for example with a slow resorbable and/or a non-resorbable bone augmenting material together with a fast resorbable material. The container can be filled for example with small particle of bone augmenting material having for example size of less than 200 microns and/or size of 200-600 microns and/or size of 500-1000 microns. The container can be filled in addition or only, for example, with large particle bone augmenting material having for example size of more than 600 microns and/or size of 1000-2000 microns and/or size of more than 2000 microns. The container can be filled for example with particles and gels.

The middle perforated region can have holes 12 which are large enough to allow bone tissue growth through these holes. The diameter of the holes can be larger than 10 microns preferably larger than 50 microns and/or larger than 100 microns and/or larger than 500 microns and/or larger than 1000 microns. The larger the holes the faster the bone regeneration. The diameter of the holes can be 500-2000 microns and/or 1000-1800 microns or larger than 2000 microns.

The holes 12 can be circular or to have any other shape. The holes 12 can occupy at least 30 percent of the surface of the middle perforated region 11. Preferably the holes 12 occupy at least 50 percent of the surface of the middle perforated region 11 and/or at least 70 percent of the surface of the middle perforated region 11 and/or at least 90 percent of the of the surface of the middle perforated region.

The middle region can have 2-10 holes and/or 10-20 holes and/or 20-50 holes and/or 50-70 holes and/or 70-100 holes and/or 100-130 holes and/or more than 130 holes. The number of holes can be determined according to the size of the middle region. The middle region can have 2-5 holes per cm$^2$ and/or 5-10 holes per cm$^2$ and/or 1-15 holes per cm$^2$ and/or 15-20 holes per cm$^2$ and/or 20-25 holes per cm$^2$ and/or more than 25 holes per cm$^2$.

The middle perforated region 11 can have holes 12 which are sized according to the bone augmenting material. For example, according to the size of the particles of the bone augmenting material and/or according to the viscosity and/or fluidity of the bone augmenting material. The diameter of the holes 12 can be less than the diameter of part of the particles of the bone augmenting material and/or less than the diameter of the majority of the particles of the bone augmenting material and/or less than the diameter of all the particles of the bone augmenting material.

The holes 12 can be larger than the diameter of the bone augmenting particles. In another embodiment the holes 12 can be larger than the diameter of the bone augmenting particles while the bone augmenting particles are inside a flowable surrounding, for example saline and/or a material that includes saline and/or blood and/or gel and/or collagen.

The filling of the container 30 can be done by pouring the bone augmenting material inside the container and/or using a spoon like device and/or using a syringe, a rigid tube, a funnel, a stick and/or any other device that can be inserted inside the container 30.

Figure 4:
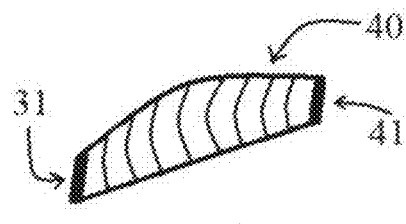
FIG. 4 is a perspective view illustrating an embodiment of the bag of FIG. 3 after the bag being filled and the other edge of the bag being closed.

After the container 30 is filled with the appropriate amount of bone augmenting material, the container 30 can be closed at the second edge 41 of the container (the container's opening through which the bone augmenting was filled) to form a closed container 40 as illustrated in FIG. 4. The closing can be for example by suturing and/or gluing with biocompatible sutures/glues. The closing of the container's opening can be also by pressure and/or heat. It is possible to fold and/or roll the container edge 41 before closing or to close it without folding and/or rolling.

The container 40 can be marketed already filled with the bone augmenting material as illustrated in FIG. 4 or to be marketed as an open container 30 as illustrated in FIG. 3 to be filled with bone augmenting material and close by the surgeon.

Figure 5:
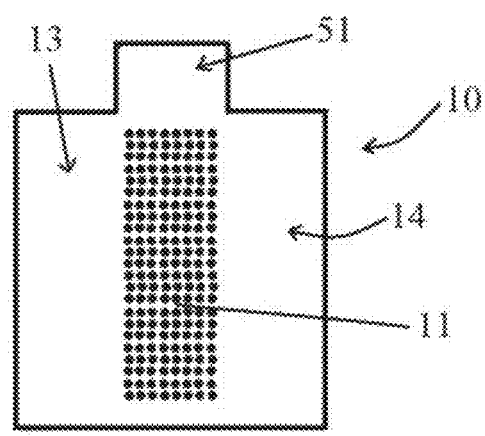
FIG. 5 is a perspective view illustrating an embodiment of a sheet having a perforated region and edge closing extension to allow easy closure of the edge of the tube, formed after folding and/or rolling the sheet.

The sheet and/or membrane 10 can include an edge closing extension 51 adjacent the middle/perforated region as illustrated in FIG. 5. This edge closing extension 51 can be used to enable easy closure of one side of the container. The sheet and/or membrane 10 can be folded and/or rolled so the first side region 13 can be placed over the middle region 11, then the edge closing extension 51 can be folded and/or rolled and placed over the first side region 13, then the second side region 14 can be placed over the first side region 13 and the edge closing extension 51. This folding and/or rolling of the sheet and/or membrane and the edge closing extension 51 can create a container 30 as illustrated in FIG. 3. The container 30 having the middle/perforated region 11 on one side of the container and two layers of membrane (the first and second side regions 13, 14) along at least part of the other side of the container forming the soft tissue blocking region 21. Adjacent the edge closing extension 51 there are three layers of membrane (the first and second side regions 13, 14 and the edge closing extension 51) along part of the soft tissue blocking region.

It is also possible that the edge closing extension 51 is folded over the middle perforated region, and the first and second side regions 13, 14 are placed over the edge closing extension 51. It is also possible that the edge closing extension 51 is folded over the first and second side regions 13, 14. The sequence and order of placing the various elements of the membrane 10 one on top of the other can be changed according to manufacturing preferences. However, if the closing extension 51 is short, it will be easier to stabilize the bag 30 while the closing extension 51 is between the side regions 13, 14.

Figure 6:
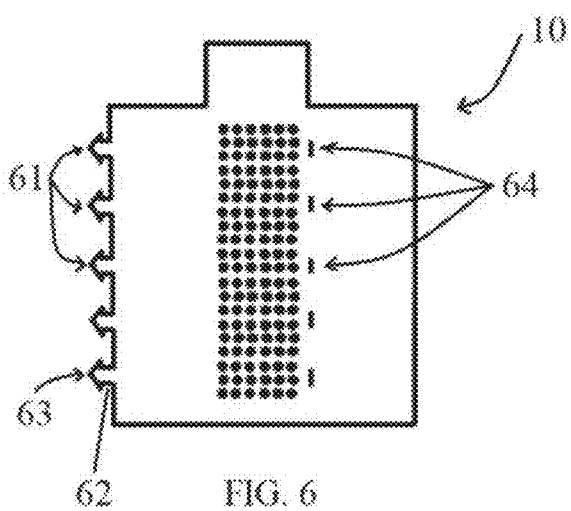
FIG. 6 is a perspective view illustrating an embodiment of a sheet having a perforated region, edge closing extension to allow easy closure of the edge of the tube formed after folding and/or rolling the sheet, connecting extensions and a slot for each connecting extension to connect the two side regions of the sheet.

The membrane 10 can have along at least part of its borders connecting extensions 61 as illustrated in FIG. 6 having connecting extensions 61 extending form one side region 13. The connecting extensions 61 can have a constant width or have an arrow shape or any other shape in which the width of the connecting extension 61 is not constant. The connecting extensions 61 can have a neck portion 62 and an anchoring portion 63 which is wider than the neck portion 62. The neck portion 62 of the connecting extension 61 being closer to the center of the membrane 10. The membrane 10 can have slots 64 so at least part of the connecting extensions 61 can be inserted through the slots 64. The length of the slots 64 can be compatible with the width of the neck portion 62 and less than the width of the anchoring portion 63 of the connecting extension 61, so after the insertion of the anchoring portion 63 through the slot 64, the anchoring portion 63 resist passing back through the slot 64 without being folded. The slots 64 can be along the folding lines 15 so as to assist also with the folding of the membrane 10. The slots 64 can be also displaced from the folding lines 15.

Figure 7:
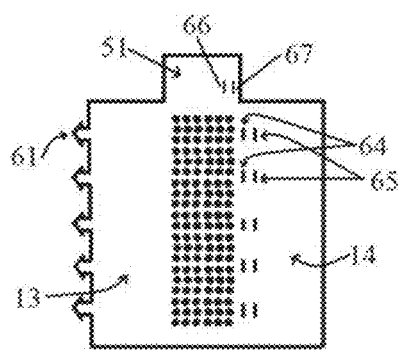
FIG. 7 is a perspective view illustrating an embodiment of a sheet having a perforated region, edge closing extension to allow easy closure of the edge of the tube, formed after folding and/or rolling the sheet, connecting extensions and two slots for each connecting extension to connect the two side regions of the sheet.
Figure 8:
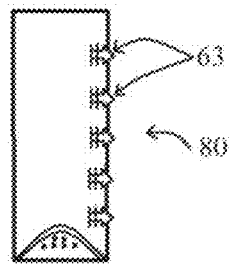
FIG. 8 is a perspective view illustrating an embodiment of a bag formed after folding and/or rolling the sheet of FIG. 7, closing one edge with the edge closing extension and connecting the side regions of the sheet using the connecting extensions inserted through the two slots.

The membrane can have two adjacent slots 64, 65 as illustrated in FIG. 7 so when the connecting extension 61 is passed through both adjacent slots 64, 65 the anchoring portion 63 will be outside the container 80 as illustrated in FIG. 8.

The closing extension 51 can have also a slot 66 or two slots 66, 67 that can be, after folding, above the slots 64, 65 in the side region 14 so the connecting extension 61 can pass through the slots 64, 65 in the side region 14 and also through the slots 66, 67 in the closing extension 51, to better stabilize the bag.

The length of the connecting extension 61 can be 1-20 mm or 2-10 mm or 3-7 mm. The membrane 10 can have more than one connecting extension or 2-10 or 3-7 connecting extensions. The distance between the connecting extensions 61 can be 2-25 mm or 3-15 mm or 5-10 mm. The connecting extensions 61 can be along both side regions 13, 14 and both side regions 13, 14 can have slots 64, 65 so each side region can be connected to the other side region. Slots can be at the middle region 11 and can be on both sides of the middle region 11.

The edge closing extension 51 can have one or more connecting extensions 61 and the first side region 13 and/or the second side region 14 can have one or more slots to fixate the edge closing extension 51 to at least one of the side region (13, 14) in a similar manner as the first side region 13 being connected to the second side region 14.

The second side region 14 can be connected to the first side region 13 and/or to the middle region 11 and/or the edge closing extension 51, so the container 80 keeps its structure and to prevent unfolding of the membrane 10. The connection between the regions of the membrane 10 can be in any manner.

Figure 9:
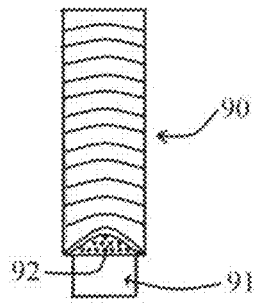
FIG. 9 is a perspective view illustrating an embodiment of a bag having one edge closed and a second edge closing extension to allow easy closure of the second edge of the bag after filling the bag.

The container 90 can have a second edge closing extension 91 adjacent the opening of the container 92 as illustrated in FIG. 9 to allow easy closure of the opening 92 of the container 90 after filling the container 90 with the bone augmenting material. The second edge closing extension 91 can be folded and/or rolled inside the container 90 or above the second side region 14 or between the first side region 13 and the second side region 14.

The membrane 10, the regions of the membrane 11, 13, 14, 51, 91, the connecting extensions 61 and the container 90 can have variable sizes and shapes, according to the bone deficiency needs to be regenerated. The membrane 10 can be for example rectangular with length of more than 60 mm or 40-60 mm or 20-40 mm or 4-20 mm or 5-17 mm and width of more than 60 mm or 40-60 mm or 20-40 mm or 4-20 mm or 5-17 mm and any combination of length and width. The container can have length of more than 60 mm or 40-60 mm or 20-40 mm or 4-20 mm or 5-17 mm. The width of the container can be more than 60 mm or 40-60 mm or 20-40 mm or 4-20 mm or 5-17 mm. The length of the container for regenerating a region of about 3 missing teeth can be 20-45 mm and the width of the container can be 7-20 mm. The length of the container for regenerating a region of about 1 missing teeth can be 5-15 mm and the width of the container can be 7-20 mm.

The closing extensions 51, 91 can have several shapes and several dimensions. The length of the closing extensions 51, 91 (along a line connecting the openings of the tube) can be 3-20 mm or 5-18 mm, or 10-15 mm or 7-10 mm or longer than 20 mm. The width of the closing extensions 51, 91 can be the same as the width of the middle region 11 or can be wider or narrower by 0.5-4 mm or 1-3 mm than the width of the middle region 11. The closing extensions can have a rectangular shape and/or have rounded corners and/or any other shape.

The middle region 11 and the side regions 13, 14 can have variable portions along the membrane 10. The middle region 11 and the side regions 13, 14 can be a third of the width of the membrane 10. The middle region 11 can be narrower than the side regions 13, 14. The side regions 13, 14 can have substantially the same width or one side region can have larger width than the other side region. The second side region can cover completely the first side region or can cover only part of the first side region. The first side region can cover completely the middle region or can cover only part of the middle region. The second side region can cover completely the middle region or can cover only part of the middle region. The width of the middle region 11 can be larger than 20 mm or 3-25 mm or 5-20 mm or 7-16 mm.

The middle region 11 can be perforated with several holes 12. The holes 12 can be along only part of the middle region 11. The edges of the middle region 11 along its width, towards the closing extensions 51, 91, can be without holes for 1-10 mm or 3-7 mm or 1-3 mm. The edges of the middle region 11 along its length, towards the first and/or second side regions 13, 14, can be without holes for 1-10 mm or 3-7 mm or 1-3 mm.

The middle region 11 can be without holes and to be bio-dissipative. The middle region 11 can bio-dissipate faster than the side regions 13, 14, which can be also non bio-dissipative. The middle region 11 can be bio-dissipative and/or to have holes. Any combination of degree of bio-dissipatedness and perforations can be.

The holes can have various combinations of sizes. For example, the middle region can have combination of large holes of more than 1000 microns with small holes of less than 500 microns.

The bone augmenting material can have various combinations of sizes. For example, the bone augmenting can have combination of large particles of more than 1000 microns with small particles of less than 500 microns. The combination of bone particles can be used with a container having a compatible combination of holes' sizes.

The bone augmenting material can have at least two bone augmenting materials having different times of resorption. For example, a fast bio-dissipative material that will allow fast ingrowth of blood vessels and bone forming cells and a slowly bio-dissipative and/or non resorbable bone augmenting material that will keep the volume for a long period of time. The slowly bio-dissipative material can be for example a bovine mineral (like Bio-Oss from Geistlich, Switzerland) that remains in the body for several years.

A slowly bio-dissipative material can be used for example also for aesthetic treatments without bone regeneration or together with bone regeneration. A container filled with slowly bio-dissipative material can be placed along the buccal aspect of the anterior maxillary alveolar ridge to increase the volume of the tissue and advance the position of the upper lip. This advance of the upper lip can eliminate wrinkles and improve the aesthetic smile and appearance. A container filled with slowly bio-dissipative material can be placed for example adjacent the zigomatic bone to advance the cheek bones. The exact position of the container can be decided for each patient according to its individual needs and according to the individual deficiency that needs to be filled.

The surgeon can prepare and insert the container through a subperiosteal tunnel or to raise a mucoperiosteal flap and suture the mucoperiosteal flap over the container. The middle region can be placed towards the bone and the side regions towards the periosteal tissue. The jaw bone can be perforated before the placement of the container adjacent the jaw bone.

In the lower jaw the preparation of the subperiosteal tunnel and/or the insertion of the container inside the tunnel can damage the mental nerve and/or its branches which are located on the buccal side of lower jaw.

Figure 10:
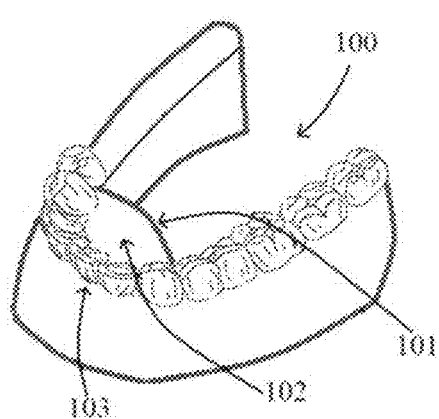
FIG. 10 is a perspective view illustrating the mandible in which the anterior lingual mucoperiosteal tissue was detached from the jaw bone to create a lingual opening to a subperiosteal tunnel.
Figure 11:
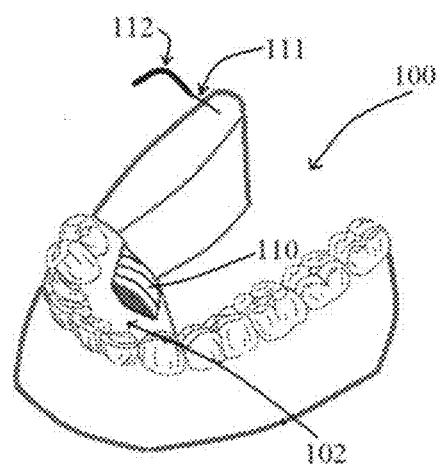
FIG. 11 is a perspective view illustrating the mandible of FIG. 10 in which a bag is inserted through the anterior lingual opening inside the subperiosteal tunnel towards the posterior region of the jaw bone.

In a novel method of using the container (or bag or pouch), at least part of the subperiosteal tunnel is prepared from the lingual side of the lower jaw as illustrated in FIGS. 10 and 11. The opening of the tunnel can be from the lingual side of the mandible (the lower jaw) 100 and in many cases from the anterior lingual side. The lingual opening 102 can be done by raising a lingual mucoperiosteal flap 101 below the anterior teeth 103 as illustrated in FIG. 10. The lingual opening 102 can be along any segment of the lingual aspect of the mandible 100 and to cross the midline of the mandible. The insertion of the container 110 can be through the lingual opening 102 as illustrated in FIG. 11. In this manner the mental nerve is not damaged. After the insertion of the container 110 it can be placed on top of the alveolar ridge to vertically augment the lower alveolar ridge and/or to be inserted and placed at the buccal and/or lingual aspects of the lower jaw bone to horizontally augment the alveolar ridge. To reach the buccal aspect, the container 110 can be pushed from the lingual side over the alveolar crest and down to the buccal side.

Before the insertion of the container 110 into the subperiosteal tunnel, it is possible to connect to the container a suture 111, which is connected to a needle 112, and to insert the needle 112 and the suture 111 inside the tunnel and to pass the needle 112 and the suture 111 through the periosteal tissue to be outside the tunnel as illustrated in FIG. 11. This way it is possible to pull the suture 111 and assist in the insertion and placement of the container inside the tunnel. The suture 111 can be sutured to the soft tissue so as to fixate the container, which is inside the tunnel. The suture 111 can be made from a bio-dissipative material.

The lingual opening 102 can be at the lingual anterior region of the lower jaw 100 and the container being placed at the posterior region of the lower jaw as illustrated in FIG. 11. The lingual opening can be at the lingual posterior region of the lower jaw and the container being placed at the anterior region of the lower jaw. The location of the lingual opening and the location of the container can be determined individually for each patient. There are advantages if the lingual opening is not above the location of the container, because if there is a later opening of the sutures at the lingual opening, it is not above the container and the chances for infection of the container are reduced. There are also advantages that the periosteal tissue above the container is not cut and sutured so the blood supply to the tissue is not damaged and therefore reducing the chances for exposure of the container.

The container (or bag or pouch) can be inserted inside the tunnel while being inside a dedicated syringe and then injecting the container to its place. This way the membrane of the container is not touching the surrounding tissues during the insertion of the container and the membrane of the container is not damaged. In another embodiment the container is inserted inside a cover and/or an envelope and/or a sleeve before being inserted inside the tunnel and after the insertion of the container the cover and/or the envelope and/or the sleeve is removed leaving the container inside the tunnel. This way the membrane of the container is not touching the surrounding tissues during the insertion of the container and the membrane of the container is not damaged. The cover and/or envelope and/or sleeve can be closed at one side to form a bag like cover with one opening. If the container is connected to a suture 111, then the suture exit the cover from the open side of the cover while the closed side of the cover is at the opposite side. In the embodiment of FIGS. 10 and 11 the closed side of the cover will be towards the anterior of the mandible. The cover can be flexible and can be made, for example, from rubber, nylon, silicon and any other materials and combinations thereof. It will be advantageous if the cover will be transparent so the surgeon will know where the perforated side of the container is. It will be advantageous if the cover bag will be made from biocompatible materials.

The container can be also fixated using a bone screw like a GBR membrane fixating screw and/or fixated by a tack or a pin like a GBR membrane fixating tack (for example, titan pin set from Botiss, Germany). The fixating inside the tunnel can be by using a curved tack delivery device (for example the AutoTac membrane fixation kit from BioHorizons U.S.). The bag can have an extension for fixation through which the bone screw and/or the bone tack will be inserted. The extension for fixation can be perforated to enable the surgeon to see the bone while inserting the screw and/or the tack. The perforated extension for fixation can be part of the perforated middle region 11 of the sheet 10 illustrated in FIGS. 1, 5, 6 and 7 after the preparing a bag, which is shorter than the perforated middle region.

The container can be stabilized by more than one tack or screw. For example, it is possible to use two tacks at the side of the bag which is close to the opening of the subperiosteal tunnel. For example, in the embodiment of FIGS. 10 and 11, the anterior (or mesial) side of the container can be fixated with one tack adjacent the anterior buccal corner of the container and a second tack adjacent the anterior lingual corner of the container. By using more than one tack (or screw) the rotation of the bag is prevented and the stabilization is improved.

It is also possible to insert through the gums at the posterior (or distal) region a fixating screw and/or a tack and/or a pin to stabilize the posterior region of the container. It is possible to perform a small cut in the posterior region of gums before the insertion of the fixating screw and/or the tack to enable the surgeon to see the container before inserting the fixating screw and/or the tack and/or to see the bone when drilling a hole for the fixating screw and/or the tack. The fixating screw and/or the tack can protrude through the gums to the oral cavity, so the gums will heal around the fixating screw and/or the tack.

The container can be used in an open sinus lift procedure called also open sinus augmentation procedure. After opening a lateral window in the lateral wall of the maxillary sinus and elevating the Schneiderian membrane, the container can be inserted through the opening in the lateral wall and to be placed above the floor of the maxillary sinus and below the elevated Schneiderian membrane. The container can be inserted already filled with bone augmenting material and/or can be filled after being inside the maxillary sinus. The container can be placed while the side with the two membranes will face the opening in the lateral wall of the maxillary sinus and/or the Schneiderian membrane and/or a tear in the Schneiderian membrane.

The container can be inserted inside the sinus in case when the Schneiderian is intact and wasn't torn during its elevation. The container can be inserted inside the sinus in cases when the Schneiderian membrane was torn during its elevation and/or in cases when the Schneiderian was damage and/or absent before the beginning of the surgical procedure. In cases when the Schneiderian membrane is torn and/or absent it is recommended to fixate the container to be in contact with the floor of the maxillary sinus. There are several options to fixate the container. For example, a dental implant and/or several dental implants can be inserted through the maxillary alveolar ridge and the floor of the maxillary sinus and inside the container. For example, the container can be fixated using screws which are used to fixate bone blocks. For example, the container can be fixated using screws or tacks which are used to fixated GBR membranes, while the screw and/or the tacks can be inserted from inside the sinus towards the oral cavity and/or from the oral cavity towards inside the sinus.

Figure 12:
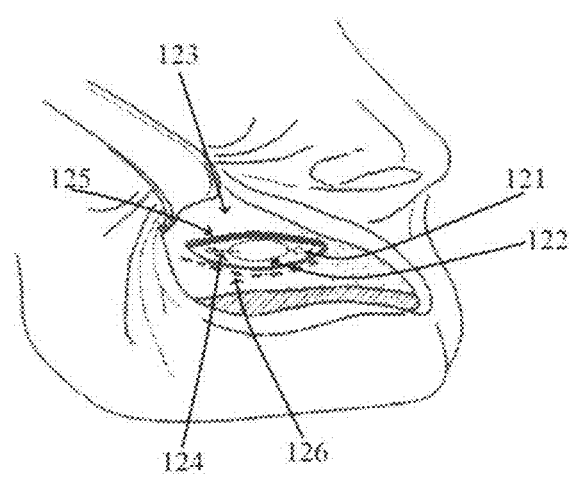
FIG. 12 is a lateral view illustrating fixating the bag inside the maxillary sinus during an open sinus lift procedure, while using sutures and/or wires and additional fixating holes.

The container can be fixated using sutures and/or wires. In one embodiment illustrated in FIG. 12, a fixating hole 121 and/or several fixating holes can be drilled adjacent to the opening 122 in the lateral wall 123 of the maxillary sinus. A suture 124 can be connected to the container 125 (the container is illustrated in FIG. 12 for clarification purposes although the container is inside the sinus and its boundaries usually can't be seen in this lateral view. In this view only the part of the container 125 which is adjacent the opening 122 can be seen) and passed through the fixating hole 121. The suture 124 can be passed through the opening 122 in the lateral wall of the maxillary. The suture can be tied and therefore fixating the container and keeping it in contact with the floor 126 of the maxillary sinus (illustrated in a dotted line in FIG. 12, the floor of the maxillary sinus usually can't be seen in this lateral view).

Usually it will be more comfortable to partially or completely fill the container after its insertion inside the maxillary sinus. In another embodiment the container can have a side opening at one of it sides—the middle region and/or the soft tissue blocking region, to enable filling the container. This filling can be in addition to filling through an opening at the edge of the bag, as described above. This filling through a side opening can be instead of filling through an opening at the edge of the bag. The bag can be marketed closed at its both edges and filled through the side opening.

The side opening can be at the soft tissue blocking region so the first (inner) sheet (or the first side region) has an opening which can be accessible through the second sheet (or the second side region). The side opening can be covered by a retractable and/or movable piece of membrane—a retractable cover, that is attached to the container and can be moved to reveal the opening to allow insertion of a bone material inside the bag and then the retractable cover can be returned to its place to close the side opening.

The side opening in the soft tissue blocking region can be covered by two retractable and/or movable pieces of membrane—retractable covers. A first retractable cover of the first (inner) sheet (or the first side region) and a second retractable cover of the second (outer) sheet (or the second side region. The second retractable cover can be larger than the first retractable cover so the borders of the second retractable cover can be over the first sheet around the borders of the first retractable cover, so the first retractable cover being partially or fully cover by the second retractable cover. This configuration can be more efficient in closing the side opening to prevent leakage of bone material from the container through the side opening.

The first and second retractable covers can be designed to be retracted to different direction. For example, the first retractable cover can be connected to the first sheet close to the right border of the container and to be retracted in the right direction, while the second retractable cover can be connected to the second sheet close to the left border of the container and to be retracted in the left direction. In another optional configuration, the first retractable cover can be connected to the first sheet closer to a first edge of the container and to be retracted towards the first edge, while the second retractable cover can be connected to the second sheet closer to the second edge of the container and to be retracted towards the second edge. This configuration of different directions of folding the retractable covers, can be more efficient in closing the side opening to prevent leakage of bone material from the container through the side opening.

The first sheet can have also a slot between the opening in the first sheet and the border of the first sheet so the second retractable cover will be inserted through this slot to better fixate the second retractable cover to prevent its dislocation during insertion of the container inside a subperiosteal tunnel. The second and/or the first retractable covers can be sutured and/or glued to the container for improved fixation. The retractable covers can have variable shapes for example, circular, oval, elliptic, rectangular and/or any tongue like shape which is connected at one side to the container.

The side opening can be adjacent to the center of the container or adjacent to the edges of the container. For augmentation of the jaw bones as described above it can be more convenient in some cases that the side opening being adjacent to one of the edges of the container. In this configuration, when both edges are already closed, the surgeon doesn't need to close the bag after filling through the side opening. For sinus lift procedures it can be more convenient in some cases that the side opening being adjacent to center of the container. One edge can be open to allow initial filling through an opening in the edge of the container and after the insertion inside the sinus the container can be filled through the side opening. If both edges of the container are closed, the initial filling and/or the filling after the insertion of the container inside the maxillary sinus can be through the side opening. In one embodiment of a container for sinus lift, the width of the middle region is smaller than the width of the side regions so the soft tissue blocking region is larger than the middle region and it is facing the Schneiderian membrane and the opening 122 in maxillary wall sinus 123 while the middle region is facing the floor 126 of the maxillary sinus. In another embodiment of a container for sinus lift, the width of the middle region is larger than the width of the side regions so the soft tissue blocking region is smaller than the middle region and it is facing the opening 122 in maxillary wall sinus 123 while the middle region is facing the floor 126 of the maxillary sinus and the Schneiderian membrane.

It is possible to place additional membrane to close the opening in the maxillary sinus, however since the bone inside the container is already covered by at least one membrane and in most places by two membranes the advantages of additional membrane are less significant.

Figure 13:
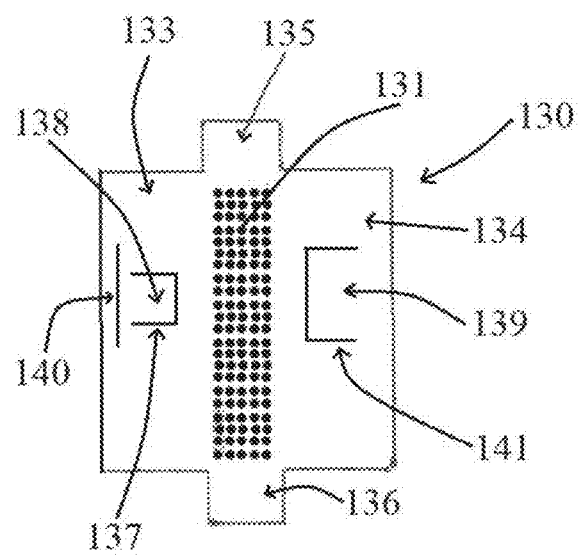
FIG. 13 is a perspective view illustrating an embodiment of a sheet having a perforated region, closing extensions and retractable covers to cover a side opening.

FIG. 13 illustrates an embodiment of a sheet and/or a membrane for preparing a container with a side opening. The sheet 130 has a middle perforated region 131 with several holes, a first side region 133, a second side region 134, a first closing extension 135 and a second closing extension 136. The sheet can include also connecting extensions and compatible slots as described above and not illustrated in FIG. 13. The first side region 133 can include a non-linear slot or several connected slots 137 surrounding partially a piece of the first side region 133 so this piece of the first side region 133 can be elevated from the first side region 133 while being connected to the first side region 133 to form a first retractable cover 138. The second side region 134 can include a non-linear slot or several connected slots 141 covering partially a piece of the second side region 134 so this piece of the second side region 134 can be elevated from the second side region 134 while being connected to the second side region 134 to form a second retractable cover 139. The first side region 133 can have also a cover fixating slot 140 to fixate the second retractable cover 139 after preparing a container from the sheet 130 and filling the container with bone augmenting material.

Figure 14:
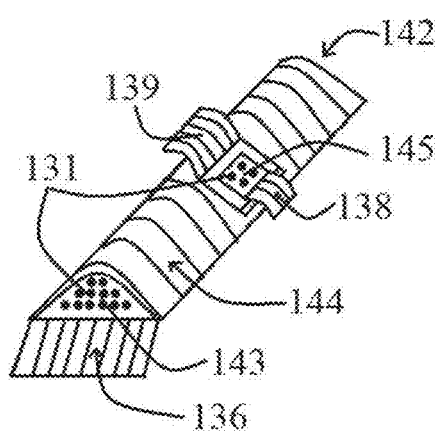
FIG. 14 is a perspective view illustrating an embodiment of a bag formed after folding and/or rolling the sheet of FIG. 13. The bag has a side opening and an edge opening to allow filling of the bag.

FIG. 14 illustrates a container 142 prepared from the membrane or sheet 130 of FIG. 13. In this embodiment one edge opening 143 is still open and the second closing extension 136 is prepared to close the edge opening 143. The second side region 134 cover the first side region 133 to form the soft tissue blocking region 144. In the soft tissue blocking region 144, the first retractable cover 138 and the second retractable cover 139 being retracted to reveal the side opening 145. The middle perforated region 131 can be seen through the edge opening 143 and through the side opening 145.

Figure 15:
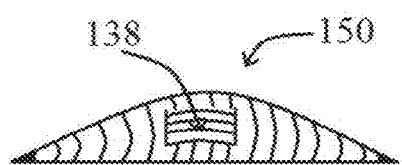
FIG. 15 is a perspective view illustrating an embodiment of the bag of FIG. 14 after the bag being filled and the edge opening closed and the side opening being covered by the two retractable covers.

FIG. 15 illustrates the container 150 after being filled and the edge opening 143 of the container of FIG. 14 being closed and the side opening 145 of the container of FIG. 14 being covered by the second retractable cover 139. The side opening 145 can be also covered by the first retractable cover 138 which is not illustrated in FIG. 15 for being covered by the second retractable cover 139. If the container is for use during a sinus lift procedure the side opening can be placed to be accessible through the opening in the maxillary sinus wall.

The container can be fixated to the floor of the maxillary sinus and/or the lateral wall of the maxillary sinus as described above, for example by using a fixating hole and sutures and/or wires. It is also possible to retract one of the retractable covers 138, 139 while leaving the other retractable cover over and closing the side opening 145. The retracted cover can be fixated to the floor of the maxillary sinus and/or the lateral wall of the maxillary sinus, for example by tacks. It is also possible to close the side openings of the container 140 of FIG. 14 without using the closing extensions 135, 136 of FIG. 13. The edges can be closed as explained above, for example by suturing. In this embodiment the closing extensions can be used to fixate the container, for example by tacks inserted through the closing extensions and the lateral wall 123 of the sinus.

The container can be used also for treatment of other tissues. For example, a similar container having holes one side can be filled with chondrocytes and place in the knee so the perforated side is towards the joint and the blocking region is towards the skin to encourage regeneration of cartilage. Similar treatment can be done in the in other joints.

The container can be placed between two tissues or organs and filled with medications that are intended for the treatment of one tissue, so the perforated side of the container will face the tissue that requires the treatment without influencing the second tissue or organ.

The sheet can be made from a materials that blocks radiation and the container can be placed between two tissues or organs and filled with a radiation emitting material that is intended for the treatment of malignancy in one tissue, so the perforated side of the container will face the tissue that requires the treatment without influencing and damaging the second tissue and/or organ. In one embodiment the sheet can be made at least partially from metal foils. In another embodiment the sheet can be made at least partially from one of the materials of guided bone regeneration membranes as mentioned above, like collagen and molecules and/or particles and/or fibers of radiation blocking material. The materials of the sheet can be bio-dissipative while the radiation blocking particles or fibers will remain without damaging the surrounding organs. Such a container can be placed for example between the prostate and the rectum while treating the prostate and protecting the rectum.

What is claimed is:

1. A device for treating patients in need of tissue regeneration comprising:
a sheet, along said sheet only a middle region has several holes with a diameter of more than 30 microns, said sheet has a first side region located at the right side of said middle region and extending from a right edge of said sheet to a first folding line between said middle region and said first side region, said sheet has a second side region located at the left side of said middle region and extending from a left edge of said sheet to a second folding line between said middle region and said left side region, said first side region has no pores or has pores such that the largest pore in said first side region has a diameter of up to 30 microns, said first side region being placed over said middle region to fully cover said middle region, said second side region being placed over said first side region to fully cover said first side region so said left edge of said sheet is adjacent said first folding line.

2. The device of claim 1, wherein said first and second side regions are forming together a soft tissue blocking region with two parallel layers covering said middle region, said soft tissue blocking region has no pores or has pores such that the largest pore in said soft tissue blocking region has a diameter of up to 30 microns.

3. The device of claim 1, wherein said middle region has more than 10 holes having diameter of 800 microns-2500 microns occupying more than 70 percent of said middle region.

4. The device of claim 1, wherein at least part of said sheet is a pericardium membrane.

5. The device of claim 1, wherein said first side region is connected to said second side region.

6. The device of claim 1, wherein said first side region has a slot and said second side region has a connecting extension, part of said connecting extension of said second side region having a width which is larger than the length of said slot in said first side region, said part of said connecting extension of said second side region being inserted through said slot in said first side region.

7. The device of claim 1, wherein a first edge of said middle region being located between said first side region and said second side region, a second edge of said middle region being located between said first side region and said second side region, said first and second edges of said middle region are located at opposite edges of said middle region, said first edge being connected to said tissue blocking region to form a bag having a filling opening adjacent said second edge of said middle region.

8. The device of claim 1, wherein an edge closing extension extends from said middle region beyond a surface of said sheet which is bounded by said first and second folding lines, said edge closing extension being placed between said first side region and said second side region to form a bag.

9. The device of claim 1, wherein an edge of said middle region is connected to said tissue blocking region to form a bag, a bone augmenting material being inside said bag.

10. A device for treating patients in need of tissue regeneration comprising:
a tube, only a first external aspect of said tube has a perforated region having several holes with diameter of more than 30 microns, said first external aspect is at the bottom of said tube, a second external aspect at the top of said tube has a soft tissue blocking region tenting over said perforated region, said soft tissue blocking region has a first sheet and a second sheet, said second sheet located on top and fully covers said first sheet to form a two layer area tenting over all said perforated region, said soft tissue blocking region has no pores or has pores such that the largest pore in said soft tissue blocking region has a diameter of up to 20 microns.

11. The device of claim 10, wherein said perforated region has more than 10 holes having a diameter of 800 microns-2500 microns.

12. The device of claim 10, wherein said first and second sheets are guided bone regeneration membranes connected by an adhesive or suture, said perforated region includes an edge closing extension, said edge closing extension being placed between said first sheet and said second sheet to form a bag.

13. The device of claim 10, wherein an entire space of said tube between said soft tissue blocking region and said perforated region being empty.

14. The device of claim 10, wherein said tube is filled with particulated bone augmenting material.

15. The device of claims 10, wherein said tube is made at least partially from a pericardium membrane.

16. A method for preparing a device for treating patients in need of tissue regeneration comprising:
   a. perforating a region of a sheet with several holes having a diameter of more than 30 microns to form a perforated region;
   b. folding a first side region of said sheet located on the right side of said perforated region above said perforated region;
   c. folding a second side region of said sheet located on the left side of said perforated region to be on top and fully cover said first side region so said first and second side regions form a two layer soft tissue blocking region tenting over all of said perforated region, said soft tissue blocking region has no pores or has pores such that the largest pore in said soft tissue blocking region has a diameter of up to 20 microns.

17. The method of claim 16, wherein said perforated region has more than 10 holes having diameter of 800 microns-2500 microns, said holes occupy more than 50 percent of said perforated region.

18. The method of claim 16, wherein said second side region has a slot and said first side region has a connecting extension, part of said connecting extension of said first side region having a width which is larger than the length of said slot in said second side region, said part of said connecting extension of said first side region being inserted through said slot in said second side region.

19. method of claim 16, wherein said folding of said first side region being along a first folding line, said folding of said second side region being along a second folding line, an edge closing extension extends from said perforated region beyond a surface of said sheet which is bounded by said first and second folding lines, said edge closing extension being placed between said first side region and said second side region to form a bag.

20. The method of claim 16, wherein said sheet is made at least partially from a pericardium membrane.

* * * * *